United States Patent [19]
Bianco et al.

[11] Patent Number: 5,782,763
[45] Date of Patent: Jul. 21, 1998

[54] ELECTROMAGNETIC BONE-ASSESSMENT APPARATUS AND METHOD

[75] Inventors: Bruno Bianco; Alessandro Chiabrera, both of Genoa, Italy; Jonathan J. Kaufman, Brooklyn, N.Y.

[73] Assignee: Cyberlogic Inc., New York, N.Y.

[21] Appl. No.: 886,323

[22] Filed: Jul. 1, 1997

Related U.S. Application Data

[62] Division of Ser. No. 459,184, Jun. 1, 1995.

[51] Int. Cl.$^6$ ..................................................... A61B 5/00
[52] U.S. Cl. .......................... 600/407; 600/408; 600/547
[58] Field of Search ................................. 600/407, 408, 600/547, 13; 324/228

[56] References Cited

U.S. PATENT DOCUMENTS

Re. 32,782  11/1988  Pratt, Jr. ................................. 128/660
3,847,141  11/1974  Hoop ........................................ 128/2

(List continued on next page.)

FOREIGN PATENT DOCUMENTS

WO 92/13485  8/1992  WIPO .

OTHER PUBLICATIONS

"Ability of Four Different Techniques of Measuring Bone Mass to Diagnose Vertebral Fractures in Postmenopausal Women" by Ott, Kilcoyne & Chestnut III, Jour. of Bone and Mineral Res., vol. 2, No. 3, 1987.

"Electrical Properties of Bone" by Singh and Saha, Biomechanic Laboratory, Department of Orthopaedic Surgery, Lousiana Sate Univ., No. 186, Jun. 1984, pp. 249–271.

"Electric and Dielectric Properties of Wet Human Cortical Bone as a Function of Frequency" by Saha and Williams, IEEE Transactions on Biomedical Engineering, vol. 39, No. 12, Dec. 1992.

"Electric and Dielectric Properties of Wet Human Cancellous Bone as a Function of Frequency" by Saha and Williams, Annals of Biomedical Engineering, vol. 17, pp. 143–158, 1989.

(List continued on next page.)

*Primary Examiner*—Marvin M Lateef
*Assistant Examiner*—Shawna J. Shaw
*Attorney, Agent, or Firm*—Dykema Gossett PLLC

[57] ABSTRACT

Non-invasive quantitative in-vivo electromagnetic evaluation of bone is performed by subjecting bone to an electrical excitation wave-form supplied to a pair of electrodes on opposite sides of a bony member, and involving a repetitive finite duration signal consisting of plural frequencies that are in the range 0 Hz–200 MHz. Signal-processing of a bone-current response signal and a bone-voltage response signal is operative to sequentially average the most recently received given number of successive bone-current and bone-voltage response signals to obtain an averaged per-pulse bone-current signal and an averaged per-pulse bone-voltage signal, and to produce their associated Fourier transforms. These Fourier transforms are further processed to obtain the frequency-dependent bone-admittance function. In a separate operation, the same electrodes respond to the same excitation signal via a medium of known electromagnetic properties and path length to establish a reference-voltage signal and reference-current signal, which are processed to produce their associated Fourier transforms. These two Fourier transforms are further processed to produce a frequency-dependent reference-admittance function, which together with the bone-admittance function are processed to derive the frequency-dependent bone-conductivity real function, $\sigma'_b(f)$, and frequency-dependent dielectric bone-permittivity real function, $\epsilon'_b(f)$. The function $\sigma'_b(f)$ is related to the energy loss in the bony member, and the function $\epsilon'_b(f)$ is related to the energy storage in the bony member. A neural network, configured to generate an estimate of one or more of the desired bone-related quantities, is connected for response to the functions $\sigma'_b(f)$ and $\epsilon'_b(f)$, whereby to generate the indicated estimates of bone status, namely, bone-density, bone-architecture, bone-strength and bone-fracture risk.

12 Claims, 10 Drawing Sheets

U.S. PATENT DOCUMENTS

| | | | |
|---|---|---|---|
| 4,105,017 | 8/1978 | Ryaby et al. | 128/1.5 |
| 4,315,503 | 2/1982 | Ryaby et al. | 128/1.5 |
| 4,361,154 | 11/1982 | Pratt, Jr. | 128/660 |
| 4,421,119 | 12/1983 | Pratt, Jr. | 128/660 |
| 4,467,808 | 8/1984 | Brighton et al. | 128/419 |
| 4,688,580 | 8/1987 | Ko et al. | 128/734 |
| 4,721,112 | 1/1988 | Hirano et al. | 128/659 |
| 4,754,763 | 7/1988 | Doemland | 128/739 |
| 4,774,959 | 10/1988 | Palmer et al. | 128/660 |
| 4,780,661 | 10/1988 | Bolomey et al. | 324/58 |
| 4,860,756 | 8/1989 | Ko et al. | 128/653 |
| 4,903,203 | 2/1990 | Yamashita et al. | 364/413 |
| 4,913,157 | 4/1990 | Pratt, Jr. et al. | 128/661 |
| 4,926,870 | 5/1990 | Brandenburger | 128/660 |
| 4,941,474 | 7/1990 | Pratt, Jr. | 128/660 |
| 4,993,413 | 2/1991 | McLeod et al. | 128/419 |
| 5,054,490 | 10/1991 | Rossman et al. | 128/661 |
| 5,259,384 | 11/1993 | Kaufman et al. | 128/660 |
| 5,318,561 | 6/1994 | McLeod et al. | 600/14 |
| 5,368,044 | 11/1994 | Cain et al. | 128/739 |
| 5,427,113 | 6/1995 | Hiroshi et al. | 128/734 |

OTHER PUBLICATIONS

"Electrical Assessment of Trabecular Bone Density: Theoretical and In Vitro Results" by Bianco, Chiabrera, Siffert and Kaufman, 42nd Annual Meeting, Orthopaedic Research Society, Feb. 19–22, 1996, Atlanta, Georgia.

ELECTROMAGNETIC BONE-ASSESSMENT APPARATUS AND METHOD

This is a divisional of copending application Ser. No. 08/459,184 filed on Jun. 1, 1995.

BACKGROUND OF THE INVENTION

The invention pertains to apparatus and method for non-invasively and quantitatively evaluating bone tissue in vivo, wherein the evaluation is manifested, at a given time, through one or more of the quantities: bone-mineral density, architecture, strength, and fracture-risk.

In recent years, various attempts have been made to use diverse forms of energy to assess the condition of bone tissue in vivo, but most often these attempts have been essentially ad hoc with no consistent framework within which to analyze data. In addition, the majority of the techniques employ signal-processing techniques that are so simple as to ignore available and useful aspects of the data; moreover, the signal-to-noise ratio of experimental data has been relatively poor. Perhaps most importantly, is that the prior techniques for bone characterization have utilized energy types for which the measurements (1) do not contain sufficient information to assess bone condition; (2) are affected significantly by non-bone related aspects (such as soft-tissue and musculature overlying the bone); (3) are subject to various measurement artifacts (such as transducer positioning, and pressure used when positioning the transducer); and/or (4) are relatively expensive to obtain.

Many prior techniques relied on ultrasonic measurements. Although significant information is obtainable from such data, ultrasound has not yet proved to be a useful tool for in vivo bone assessment. Ultrasonic techniques are highly sensitive to positioning of the transducers. Low-frequency vibrational measurements have also been proposed for assessing bone, but these have also not led to any practical clinical devices. In particular, vibrational measurements are strongly affected by soft tissue overlying the bone, as well as positioning and coupling the transducers to the skin.

Apparatuses which utilize ionizing electromagnetic radiation have also been developed and are currently used clinically to assess bone in vivo to provide estimates of bone mineral density. However these devices are relatively expensive, measure bone mass only (and not bone architecture, strength, and/or fracture risk), and expose the patient to ionizing radiation. A review of these radiation based methods may be found in the article by Ott et al., in the *Journal of Bone and Mineral Research*, Vol. 2, pp. 201–210, 1987.

Electrical (non-ionizing) impedance measurements have been applied for a variety of basic research purposes, but as of yet have apparently not been suggested as a means for clinical (in vivo) bone assessment in bone loss diseases, such as osteoporosis. Thus, we are disclosing for the first time method and apparatus for the use of non-ionizing electromagnetic measurements to assess bone in vivo, as a means for non-invasively determining the degree of osteoporosis in an individual, as represented by one or more of the following quantities: density, architecture, strength, and fracture risk.

U.S. Pat. No. 3,847,141 to Hoop discloses a device to measure bone density as a means of monitoring calcium content of the involved bone. A pair of opposed ultrasonic transducers is applied to opposite sides of a patient's finger, such that recurrent pulses transmitted via one transducer are "focused" on the bone, while the receiving response of the other transducer is similarly "focused" to receive pulses that have been transmitted through the bone. The circuitry is arranged such that filtered reception of one pulse triggers the next pulse transmission; the filtering is by way of a bandpass filter, passing components of received signals, only in the 25 to 125 kHz range; and the observed frequency of retriggering is said to be proportional to the calcium content of the bone.

Pratt, Jr. is identified with a number of U.S. patents, including U.S. Pat. Nos. 4,361,154, 4,421,119 (divisionally related to the '154 patent, and subsequently reissued, as U.S. Pat. No. Re. 32,782), U.S. Pat. Nos. 4,913,157, and 4,941,474, all dealing with establishing, in vivo, the strength of bone in a live being such as a horse. In the first three of his patents, the inventor bases his disclosures on the measurement of transit time from "launch" to "reception" of pulses of 0.5 MHz and 1.0 MHz through the bone and soft tissue, and from measurement of pulse-echo time, to thereby derive a measurement of transit time through bone alone. A data bank enables his evaluation of the meaning of variations in measurements of transit time, which the inventor deduces to be propagation velocity through each measured bone. The inventor's U.S. Pat. No. 4,913,157 operates on the same general principle of transit-time/velocity deduction, using the later preferred frequency of 2.25 MHz as the base frequency of pulsed "launchings", and he purports to derive the bone-transfer function from analysis of an average of received pulses. In his U.S. Pat. No. 4,941,474, the inventor further refines his technique of transit-time/velocity deduction, inter alia, by separately determining the ratio of the velocity of his observed "bone signal" to the velocity of his observed "soft-tissue signal", using the technique of matched filtering/Fourier transform filtering set forth in his U.S. Pat. No. 4,913,157.

Palmer, et al., U.S. Pat. No. 4,774,959 discloses apparatus for deriving the slope of the relation between ultrasonic frequency and attenuation, for the case of a sequence of tone signals, in the range 200 to 600 kHz, applied to one transducer and received by another transducer, (a) after passage through a heel bone, in comparison with (b) passage between the same two transducers without the intervening presence of the heel. The assumption necessarily is that the frequency/attenuation relation is a straight line, i.e. of constant slope.

Brandenburger, U.S. Pat. No. 4,926,870 discloses another in vivo bone-analysis system which depends upon measuring transit time for an ultrasonic signal along a desired path through a bone. A "Canonical" wave form, determined by previous experience to be on the correct path, is used for comparison against received signals for transmission through the patient's bone, while the patient's bone is reoriented until the received signal indicates that the patient's bone is aligned with the desired path. Again, ultrasonic velocity through the patient's bone is assumed to have been determined from measured transit time.

Rossman, et al., U.S. Pat. No. , 5,054,490 discloses an ultrasound densitometer for measuring physical properties and integrity of a bone, upon determination of transit time, in vivo, through a given bone, in comparison with transit time through a medium of known acoustic properties; alternatively, the Rossman, et al. device compares absolute attenuation of specific frequency components of ultrasound acoustic signals through the bone with the absolute attenuation of the same frequency components through a medium of known acoustic properties. For attenuation measurements, a "broad-band ultrasonic pulse" is recommended and is illustrated as a single spike "which resonates with a broadband ultrasonic emission". The necessary comparisons are performed by a microprocessor, resulting in a slope of attenuation versus frequency in the broadband of interest. The frequencies or frequency ranges are not disclosed.

Kaufman et al., U.S. Pat. No. 5,259,384 disclose method and apparatus for ultrasonically assessing bone tissue. A composite sine wave acoustic signal consisting of plural discrete frequencies within the ultrasonic frequency range to 2 MHz are used to obtain high signal-to-noise ratio of the experimental data. A polynomial regression of the frequency-dependent attenuation and group velocity is carried out, and a non-linear estimation scheme is applied in an attempt to estimate the density, strength, and fracture risk of bone in vivo.

Doemland, U.S. Pat. No. 4,754,763 discloses a noninvasive system for testing the integrity of a bone in vivo. He uses low-frequency mechanical vibrations to characterize the state of healing in a fractured bone. The frequency response is used to classify the stage of healing.

Cain et al., U.S. Pat. No. 5,368,044 applied a similar method, namely, low-frequency mechanical vibrations, to assess the state or stiffness of bone in vivo. The method evaluates the peak frequency response or a cross-correlation of the frequency vs. amplitude response.

Brighton et al., U.S. Pat. No. 4,467,808 discloses method for preventing and treating osteoporosis in a living body by applying electrical stimulation non-invasively. They supply about 5–15 volts peak-to-peak at a single frequency within the range of about 20–100 kHz to cause a "treatment current" to flow in the bony part afflicted by osteoporosis.

Numerous other patents disclose methods for stimulating bone growth which rely on the application of electromagnetic signals to the body. For example, Ryaby et al. U.S. Pat. Nos. 4,105,017 and 4,315,503 describe methods for promoting bone healing in delayed and nonunion bone fractures, using an asymmetric pulsed waveform. In U.S. Pat. No. 4,993,413, McLeod et al. disclose method and apparatus for inducing a current and voltage in living tissue to prevent osteoporosis and to enhance new bone formation. They disclose the use of a symmetrical low frequency and low intensity electromagnetic signal substantially in the range of 1–1000 Hertz. In Liboff et al., U.S. Pat. No. 5,318,561 (and others), methods are disclosed which incorporate the combined use of a static and time-varying magnetic field to stimulate bone healing and growth. Specific amplitudes and frequencies are disclosed for optimal enhancement of bone growth, based on the theory of "ion-cyclotron resonance."

In several papers, including a review article, Saha et al. report on the electrical properties of bone. In "Electrical Properties of Bone," in *Clinical Orthopaedics and Related Research*, No. 186, June 1984, pp. 249–271, by Singh and Saha, they state that the electrical conductivity and permittivity of bone are frequency-dependent, reviewing data of various researchers in the 0–1 MHz frequency range. In two more recent papers, namely, "Electric and Dielectric Properties of Wet Human Cortical bone as a Function of Frequency," *IEEE Transactions on Biomedical Engineering*, Vol. 39, No. 12, December 1992, pp. 1298–1304, and "Electric and Dielectric Properties of Wet Human Cancellous Bone as a Function of Frequency," *Annals of Biomedical Engineering*, Vol. 17, pp. 143–158, 1989, both by Saha and Williams, they reported on the resistance and capacitance of in vitro bone samples in the frequency range 120 Hz to 10 MHz. They also studied the directional dependence of the measured impedance, and found that bone was electrically anisotropic. They also presented in vitro data on 30 cancellous bone samples which demonstrated a relatively small linear correlation (r=0.63) between specific capacitance and wet density.

The prior art, exemplified by the references that have been briefly discussed, have had little success in providing a simple, relatively inexpensive device or method for clinical non-invasive assessment of bone. They have focussed primarily on mechanical (low-frequently vibrational or ultrasonic) means, which thus far has not led to a useful clinical tool, or on much more expensive X-ray densitometers, which measure bone mass alone, with their associated ionizing radiation. On the contrary, electromagnetic measurements, although the subject of several academic in vitro investigations, have apparently been completely overlooked as a potential clinical tool for non-invasively assessing bone in vivo in bone loss diseases such as osteoporosis. In fact, the electrical parameters of bone have been investigated solely for their use in evaluating the currents and voltages induced by specific exogenous therapeutic or environmental electromagnetic fields. In the relatively few (in vitro) studies which considered the biophysical properties of bone in relation to electromagnetic measurements, no analytic framework was used, a broad frequency range was not used, and no attempt to develop a non-invasive clinical in vivo electromagnetic apparatus and/or method for assessing osteoporosis, with respect to bone-mineral density, architecture, strength and fracture risk, has previously been disclosed.

BRIEF STATEMENT OF THE INVENTION

It is accordingly an object of the invention to provide an improved method and apparatus for non-invasive and quantitative evaluation of bone tissue in vivo.

Another object is to meet the above object, such that bone-mineral density, architecture, strength, and fracture risk may be readily and more reliably evaluated than heretofore.

A specific object is to achieve the above objects with a broadband electromagnetic approach wherein the signal sufficiently exceeds noise throughout the broadband, to enable evaluation of received signal above noise, throughout the broadband spectral region, from 0 Hz to 200 MHz.

It is a general object to achieve the foregoing objects with apparatus components that are for the most part commercially available.

Briefly stated, the invention in its presently preferred form achieves the foregoing objects by iteratively subjecting bone to a finite time duration electrical voltage excitation signal, applied through a current measuring resistor to two electrodes on opposite sides of the bone, and involving a pulsed repetitive signal that has frequency components in the spectral region from 0 Hz to 200 MHz; the voltage excitation signal is repeated substantially in the range 1 to 10000 Hz. Signal-processing of the measured voltage response signal across the two electrodes together with the electrical current response signal through the two electrodes is operative (a) to sequentially average the most recently received given number of successive bone-voltage and bone-current response signals to obtain associated averaged per-pulse bone-voltage and bone-current response signals and (b) to produce Fourier transforms of the averaged per-pulse bone-voltage response and bone-current response signals. The Fourier transform of the averaged per-pulse bone-current response signal is then divided by the Fourier transform of the averaged per-pulse bone-voltage response signal to obtain a capacitively-determined bone-admittance function (or equivalently, a capacitively-determined bone-impedance function or a capacitively-determined bone-reflection-coefficient function). In a separate operation not involving the bone the same electrodes, with an identical electrode spacing as used to measure the bony member, and same voltage excitation signal are used to measure a medium of known electromagnetic properties. This is carried out to establish a reference-voltage response signal and a reference-current response signal, and these reference signals are respectively signal-processed to produce their associated Fourier transforms. The Fourier transform of the reference-current response signal is then divided by the Fourier transform of the reference-voltage response signal to obtain the capacitively-determined reference-admittance function (or equivalently, a capacitively-determined reference-impedance function or a capacitively-determined reference reflection-coefficient function). The two admittance functions are processed to derive the capacitively-determined frequency-dependent dielectric bone-permittivity real function, $\epsilon'_{E,b}(f)$, and the capacitively-determined frequency-dependent electrical bone-conductivity real function, $\sigma'_{E,b}(f)$, associated with the bony member; specifically, the bone-permittivity function, $\epsilon'_{E,b}(f)$, is related to the energy storage of the electromagnetic field within the bony member, and the bone-conductivity function, $\sigma'_{E,b}(f)$, is related to the energy loss within the bone tissue. Finally, a neural network, configured to generate an estimate of one or more of the desired bone-related quantities, is connected for response to the bone-conductivity function, $\sigma'_{E,b}(f)$, and to the bone-permittivity function, $\epsilon'_{E,b}(f)$, whereby to generate the indicated estimates of the status of bone that is being analyzed.

BRIEF DESCRIPTION OF THE DRAWINGS

The invention will be described in detail for a presently preferred embodiment, in conjunction with the accompanying drawings, in which.

DETAILED DESCRIPTION OF THE INVENTION

The invention will be described in detail for a presently preferred embodiment, in conjunction with the accompanying drawings.

Figure 1:
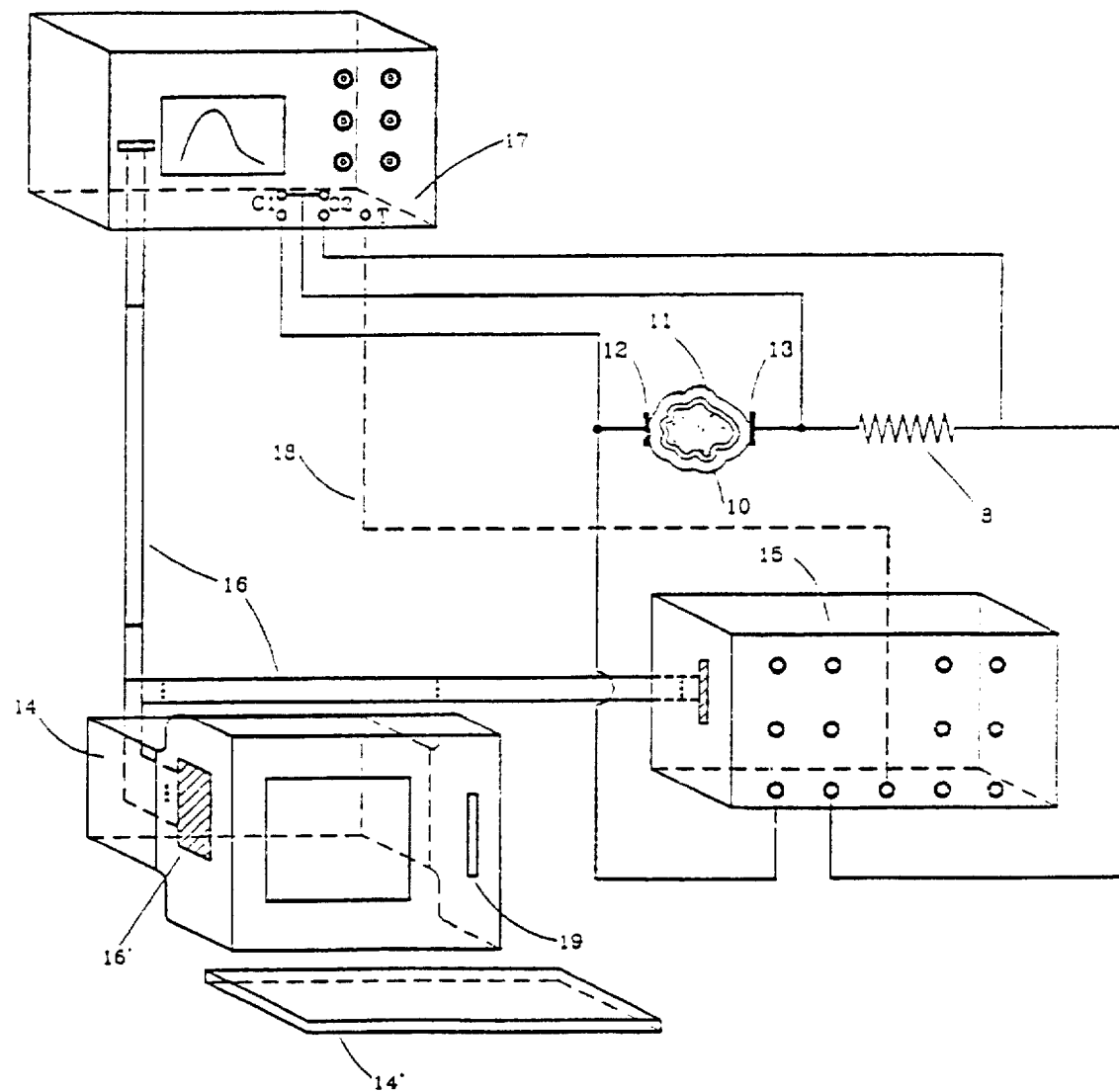
FIG. 1 is an electrical-circuit diagram schematically showing the interconnected relation of components of apparatus of the invention.

The invention is shown in FIG. 1 in application to interconnected components for constructing apparatus for performing methods of the invention, namely, for non-invasively and quantitatively evaluating the status of bone tissue in vivo, as manifested through one or more of the quantities: bone-mineral density, architecture, strength, and fracture risk at a given time. These components are, in general, commercially available from different sources and will be identified before providing detailed description of their total operation.

In FIG. 1, the bone locale 10 to be analyzed in vivo is shown surrounded by soft tissue 11 and to be interposed between two aligned and opposed capacitive-type electrodes 12, 13, which may be identically the same, and each consisting of a 1 cm radius circular Copper plate; suitably, each of electrodes 12, 13 may be simply constructed from a sheet of Copper available from any general hardware store. As shown, electrodes 12, 13 are used to generate electromagnetic fields within the bone 10 and its surrounding soft tissue 11. A conducting paste (not shown) is used to ensure good electrical contact between the electrodes and the skin. An electronic caliper, also not shown, most suitably a Mitutoyo Model No. 610-0038, available from Eastern Tool and Supply Co., (New York, N.Y.), may be used to measure the separation distance between the electrodes.

Basic operation is governed by computer means 14, which may be a PC computer, such as the "P5-90" available from Gateway 2000, Inc., North Sioux City, S. Dak.; as its designation suggests, this computer contains a 90 MHz clock-pulse generator, and an Intel Pentium processor, with provision for keyboard instruction at 14'.

An arbitrary function-generator 15 is shown and is relied upon to generate a voltage excitation signal, v(t), which is periodically supplied through a current measuring resistor 8 to the two electrodes 12, 13.

The voltage excitation signal generated by function-generator 15 is a finite-duration signal, comprised of plural frequencies that are contained in the spectral region from 0 Hz to approximately 200 MHz, and this excitation signal is repeated substantially in the range 1 to 20,000 Hz. Generator 15 may suitably be an arbitrary function-generator (waveform-synthesizer) product of Tektronix, Inc., Beaverton, Or. identified by Tektronix Model No. AWG 2040. This waveform synthesizer provides generation of analog signals independent of the host computer 14, allowing full processor power to be used for other tasks, including calculation of waveform data; it has the capacity to generate an output signal comprising literally millions of points (with Option #01) in the indicated electromagnetic frequency region.

A digital storage oscilloscope 17 is also shown in FIG. 1 and is used for converting two signals into digital format for further processing in computer 14, namely the voltage-response signal measured across electrodes 12, 13, and the current-response signal measured across the current measuring resistor 8. Oscilloscope 17 may suitably be a 1 GHz sampling rate two-channel waveform digitizer, Model No. DSA 601A, a product available from Tektronix, of Beaverton, Or. The oscilloscope 17 is supplied with two identical differential plug-in amplifiers (Part #11A33) and is used to acquire the voltage-response and current-response signals, as shown in FIG. 1. A connection 18 is shown by dashed lines, connecting the function-generator 15 to the oscilloscope 17, for synchronizing purposes and for the purposes of digitizing the excitation signals, to enable computer 14 to perform a suitably compensated, continuously operative updating average of the response signals measured across electrodes 12 and 13 and simultaneously across the current measuring resistor 8. Computer control of both the digitizing oscilloscope 17 and of the function-generator 15 is enabled via the General Purpose Interface Bus (GPIB) 16, and a GPIB card 16' in the computer 14. The GPIB 16 and GPIB card 16' may suitably be obtained from National Instruments, Inc., Austin, Tex.

Finally, general signal-processing/display/storage software, for the signal-processing control and operation of the computer is not shown but will be understood to be a floppy disk loaded at 19 into the computer; this software is suitably the MATLAB for Windows, available from The Math Works, Inc., Natick, Mass. This software includes the Neural Network and Signal Processing Toolboxes. Further software, also not shown but loaded into the computer, is least-squares regression modeling software, identified as TableCurve, a product of Jandel Scientific, Inc., San Rafael, Calif. and a Fortran language compiler, available from Microsoft Corporation, Beaverton, Oreg., and GPIB communications software available from National Instruments, Austin, Tex.

In the presently preferred embodiment, involving the described components of FIG. 1, the same components are utilized not only for performing the continuously updated averaging of the latest succession of response signals measured across 12, 13, and across 8, but also for establishing and entering into computer storage reference-voltage and reference-current response signals that are obtained by removing the body part 10, 11 from the space between capacitive electrodes 12, 13. These reference signals will be further signal-processed in the computer to obtain their associated Fourier transforms. The Fourier transform of the reference-current response signal is then divided by the Fourier transform of the reference-voltage response signal, to obtain the capacitively-determined reference-admittance function, $Y_{E,r}(f)$. Computer operation on the updated average of the bone-voltage and bone-current response signals will be referred to as the averaged per-pulse bone-voltage response signal and averaged per-pulse bone-current response signal, and these averaged per-pulse bone-response signals are also signal-processed in the computer into their respective Fourier transforms. The Fourier transform of the averaged per-pulse bone-current response signal is then divided by the Fourier transform of the averaged per-pulse bone-voltage response signal, to obtain the capacitively-determined bone-admittance function, $Y_{E,b}(f)$.

The computer will be understood to be further programmed to process the capacitively-determined bone-admittance and reference-admittance functions, thereby producing the capacitively-determined frequency-dependent dielectric bone-permittivity real function, $\epsilon'_{E,b}(f)$, and the capacitively-determined frequency-dependent electrical bone-conductivity real function, $\sigma'_{E,b}(f)$, associated with the bony member. Finally, these two functions, for each of the large plurality of involved frequencies in the input excitation signal, are supplied within the computer to the neural network, it being understood that the neural network will first have been configured and trained to generate an estimate of one or more of the above-indicated and currently analyzed bone properties, namely, bone-mineral density, architecture, strength, and fracture risk.

Figure 2:
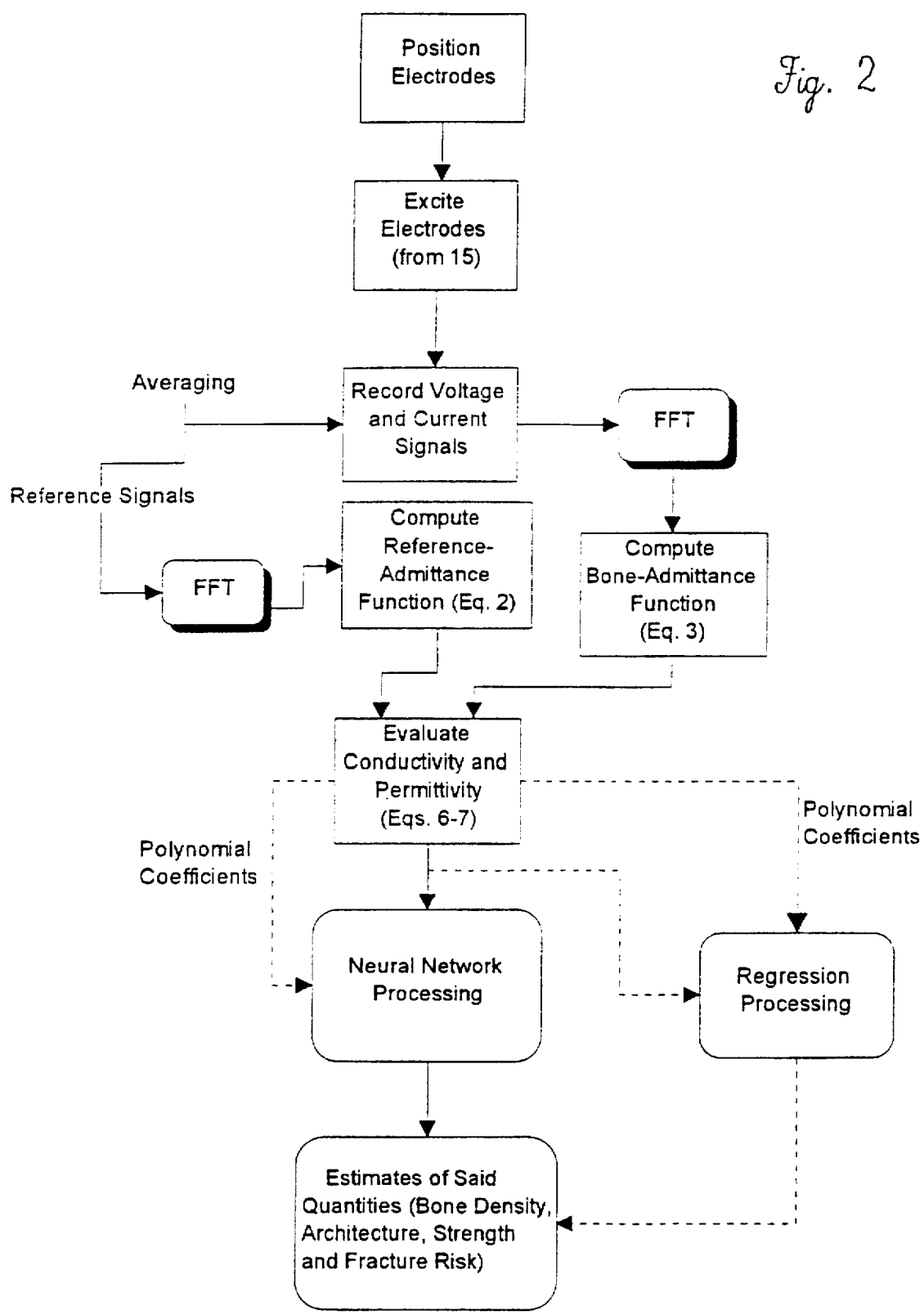
FIG. 2 is a flow chart of computer-controlled operations associated with FIG. 1, in automatically analyzing and quantitatively reporting estimates of relevant bone properties.

In the presently preferred embodiment of the invention and with additional reference to the flow diagram of FIG. 2, data is collected and processed as follows. A bony member (10, 11) is placed between two capacitive-type electrodes (12, 13). An electrical voltage excitation or input signal is applied through a current measuring resistor (8) to the two electrodes (12, 13) and generates an electromagnetic field in the bony member (10, 11). The electrical input signal is generated using a finite-duration signal. The applied waveform, v(t), is described by $$v(t) = \sum_{i=0}^{N} p(t - iT_p), \quad 0 \leq t \leq T \quad (1)$$

where p(t) is a single repetition of the applied excitation signal, $T_p$ is the time interval over which p(t) is defined and is the inverse of the pulse repetition rate, N+1 is the total number of repetitions of the waveform p(t), and T is the total time of application of the excitation signal. In this preferred embodiment, p(t) is a square pulse of width $\tau=10$ ns, $T_p=10$ ms, N=1023, and T=10.24 s. This particular choice of application signal provides for finite energy throughout the specified spectral domain so that the measurements have sufficient signal-to-noise ratio throughout the desired frequency range. Other choices of waveform are possible as well, such as sinusoidal inputs.

Each repetition, p(t), of the above excitation signal is applied periodically at a rate of 100 Hz. In the presently preferred embodiment, the $i^{th}$ repetition associated with the input excitation signal is associated with two response waveforms, namely, the bone-voltage response signal, $v_{b,i}(t)$, and the bone-current response signal, $i_{b,i}(t)$. These response signals are averaged a total of N+1=1024 times to obtain the averaged per-pulse bone-voltage response signal, $v_b(t)$, and the averaged per-pulse bone-current response signal, $i_b(t)$. Subsequently, the Discrete Fourier Transforms (DFT), $V_b(f)$ and $I_b(f)$, of $v_b(t)$ and $i_b(t)$, respectively, are obtained using the Fast Fourier Transform (FFT) algorithm. The Fourier transforms are all evaluated at a discrete set of frequencies, $f_i$, i=1, ..., K, and in this embodiment K=18, $f_1$=200 Hz, $f_2$=500 Hz, $f_3$=1200 Hz, $f_4$=2000 Hz, $f_5$=5000 Hz, $f_6$=10,000 Hz, $f_7$=15,000 Hz, $f_8$=25,000 Hz, $f_9$=40,000 Hz, $f_{10}$=80,000 Hz, $f_{11}$=125 kHz, $f_{12}$=200 kHz, $f_{13}$=350 kHz, $f_{14}$=650 kHz, $f_{15}$=1 MHz, $f_{16}$=2 MHz, $f_1$=5 MHz and $f_1$=10 MHz. Not shown explicitly but to be understood is that the signal measured across the current measuring resistor 8 (Channel 2 of the digital oscilloscope 17 in FIG. 1) is divided by the value of the resistor [in ohms (Ω)], which in this presently preferred embodiment is equal to 100 Ω.

Two averaged per-pulse reference signals, the averaged per-pulse reference current response, $i_r(t)$, and the averaged per-pulse reference voltage response, $v_r(t)$, are also obtained by averaging each of 1024 reference-current and reference-voltage response signals produced with air only between the two electrodes, i.e., by removing the bony member and carrying out the entire measurement procedure with air separating the two transducers. The same input excitation signal is used for generation of these reference signals, with the same electrode spacing as that used for the bony member. The DFT's, $V_r(f)$ and $I_r(f)$, of the averaged per-pulse reference voltage response and the averaged per-pulse reference current response signal are then obtained using the FFT.

The data is further processed to obtain the capacitively-determined reference-admittance function, $Y_{E,r}(f)$, and the capacitively-determined bone-admittance function, $Y_{E,b}(f)$. Specifically, $$Y_{E,r}(f) \triangleq \frac{I_r(f)}{V_r(f)} \tag{2}$$

and $$Y_{E,b}(f) \triangleq \frac{I_b(f)}{V_b(f)} \tag{3}$$

Then $Y_{E,b}(f)$ and $Y_{E,r}(f)$ are processed further to obtain the capacitively-determined frequency-dependent dielectric bone-permittivity real function, $\epsilon'_{E,b}(f)$, and the capacitively-determined frequency-dependent electrical bone-conductivity real function, $\sigma'_{E,b}(f)$, associated with the bony member. In particular, $$Y_{E,r} = j\omega \epsilon_o F \tag{4}$$

where $\epsilon_o = 8.85 \times 10^{-12}$ F/m and $\omega = 2\pi f$ are the dielectric permittivity of free space and radian frequency, respectively, and $$Y_{E,b}(f) = \sigma'_{E,b} F + j\omega \epsilon'_{E,b} F \tag{5}$$

In Eqs. (5) and (6), F is a geometric form factor which remains approximately constant for both the bone tissue and reference (air) measurements. The real conductivity and real permittivity of the bony member can then be found as follows:

$$\sigma'_{E,b}(f) = -Im \left[ \frac{Y_{E,b}(f)}{Y_{E,r}(f)} \right] 2\pi f \epsilon_o \tag{6}$$

and $$\epsilon'_{E,b}(f) = \epsilon_o Re \left[ \frac{Y_{E,b}(f)}{Y_{E,r}(f)} \right] \tag{7}$$

where Re and denote the real and imaginary parts, respectively.

The capacitively-determined frequency-dependent electrical bone-conductivity real function, $\sigma'_{E,b}(f_i)$, i=1, . . . , K, and the frequency-dependent dielectric bone-permittivity real function, $\epsilon'_{E,b}(f_i)$, i=1, . . . , K, serve as inputs into an appropriately configured neural network to generate an estimate of one or more of the above-indicated and currently analyzed bone properties, namely, bone-mineral density, architecture, strength, and fracture risk. In the presently preferred embodiment, the neural network is a feedforward network with 36 inputs (corresponding to 18 inputs each of the capacitively-determined electrical conductivity and dielectric permittivity functions at the chosen set of frequencies), 1 (bone density) output, and one hidden layer which consists of 50 processing elements. The network is trained with the backpropagation algorithm to estimate bone mineral density. The neural network nonlinearly combines in an optimal least-squares fashion the information contained in the electrical conductivity and dielectric permittivity functions in estimating the desired bone property, in this case bone density. Importantly, this neural network approach does not require any a priori information on the functional form relating the bone-conductivity and bone-permittivity functions to density (or architecture, strength or fracture-risk). It extracts this information from the data itself.

In a variation of the described procedure, both the frequency-dependent electrical bone-conductivity, $\sigma'_{E,b}(f_i)$, i=1, . . . , K, and the frequency-dependent dielectric bone-permittivity, $\epsilon'_{E,b}(f_i)$, i=1, . . . , K, are modeled with polynomials whose coefficients are obtained using linear-least-squares regression analysis. These coefficients, i.e. , $\sigma'_{E,b0}, \sigma'_{E,b1}, \ldots, \sigma'_{E,bQ}$ and $\epsilon'_{E,b0}, \epsilon'_{E,b1}, \ldots, \epsilon'_{E,bR}$, serve as inputs to another appropriately configured neural network. In this alternative preferred embodiment, Q=R=2 (i.e., quadratic curve-fitting), and the neural network is a feedforward network with 6 inputs (corresponding to three inputs each for the conductivity and permittivity, respectively), 1 (bone density) output, and 1 hidden layer consisting of 16 processing elements. The neural network can also be configured to estimate bone architecture, bone strength and/or fracture risk, in addition to bone density. In these cases, different sets of training data are required to train the neural network.

In certain applications to bone diagnosis, it may be possible to achieve sufficient accuracy and precision with univariate or multivariate regression functions in place of a neural network. In one such alternative embodiment, a second-order multivariate regression is used which employs the frequency-dependent bone-conductivity and dielectric bone-permittivity functions of the bony member as the independent variables and the bone density as the dependent variable. Another alternative embodiment employs the regression coefficients of the conductivity and permittivity as the independent variables, and the desired bone property as the output or dependent variable of the multivariate regression. For example, an analytic representation of this embodiment is given by $$\rho = a_0 \sigma'_{E,b0} + a_1 \sigma'_{E,b1} + a_2 \sigma'_{E,b2} + b_0 \epsilon'_{E,b0} + b_1 \epsilon'_{E,b1} + b_2 \epsilon'_{E,b2} \tag{8}$$

where $\rho$ is the desired bone density value, and $a_i$ and $b_i$, i=0,1,2, are regression coefficients obtained through standard least-squares analysis. These various alternative embodiments are depicted in the flow diagram of FIG. 2.

Figure 3:
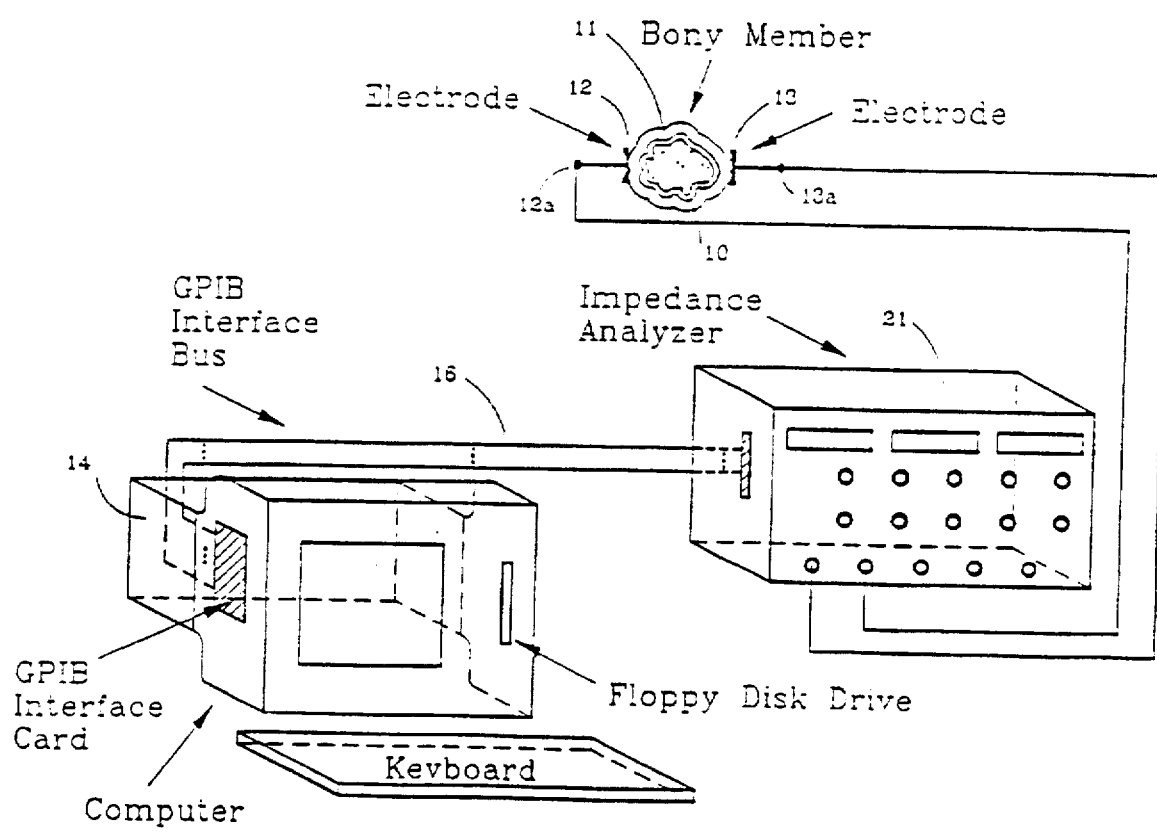
FIG. 3 is an electrical-circuit diagram schematically showing the interconnected relation of components of apparatus of the invention, but for another embodiment.

In an alternative embodiment of the invention and with additional reference to FIG. 3, an electrical impedance analyzer is used to obtain the admittance data associated with the bony member. In this case, terminal 12a of electrode 12 and terminal 13a of electrode 13 are connected to an impedance analyzer 21 to evaluate the bone-admittance function. The impedance analyzer may suitably be a Hewlett-Packard (Santa Clara, Calif.) Model No. 4192A.

Figure 4:
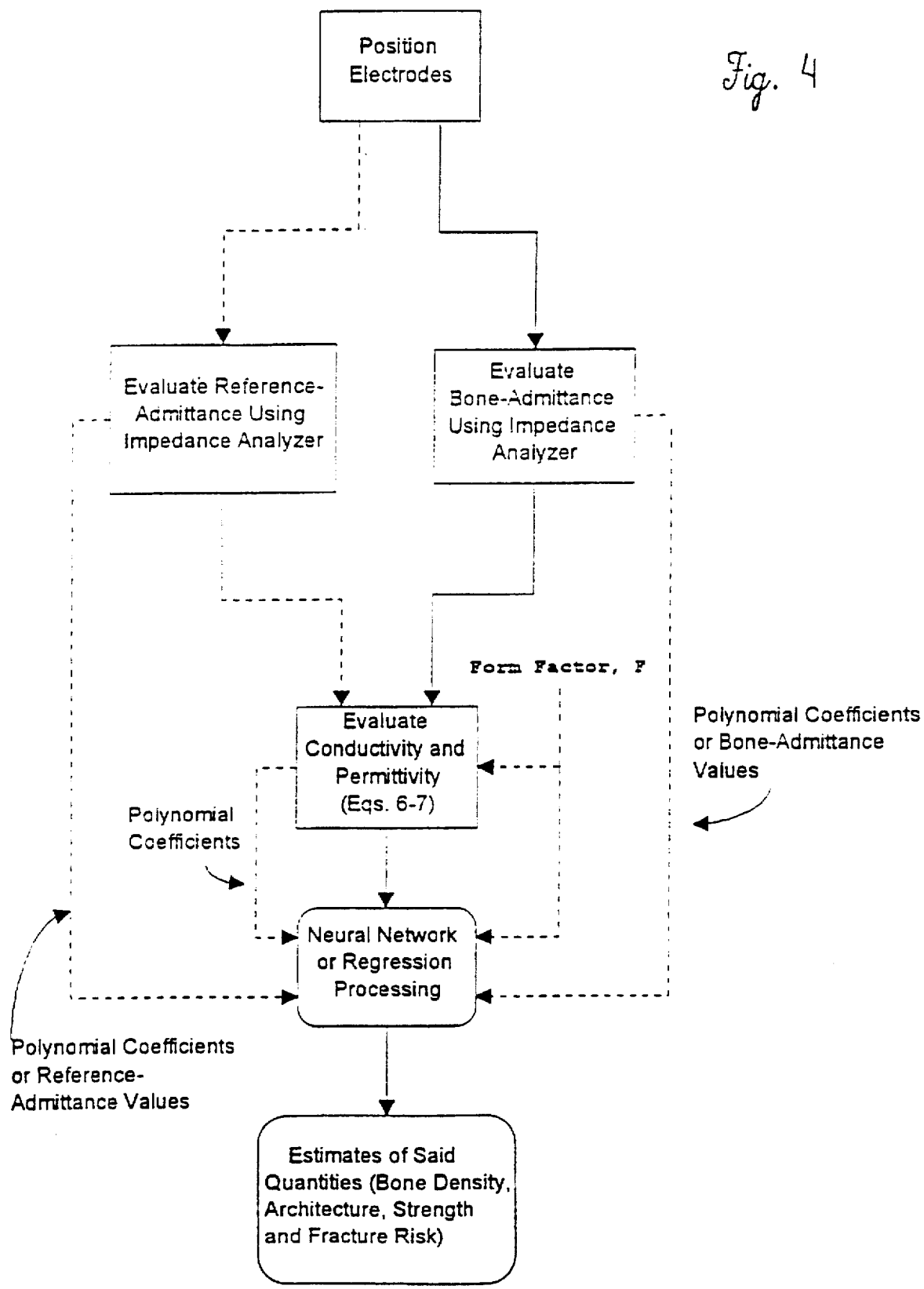
FIG. 4 is a flow chart of computer-controlled operations associated with FIG. 3, in automatically analyzing and quantitatively reporting estimates of relevant bone properties.

This impedance analyzer provides bone-admittance function data over a frequency range of 5 Hz–13 MHz, and is connected via a general purpose interface bus (GPIB), 16, to a personal computer 14. A reference-admittance function is also obtained by removing the bony member 10,11, from between the electrodes (with air only between the electrodes) and repeating the measurements with the impedance analyzer. The bone-admittance function data, $Y_{E,b}(f)$, and reference-admittance data, $Y_{E,r}(f)$, as evaluated by the impedance analyzer are transferred (i.e., downloaded over the GPIB 16) to the personal computer 14 for processing identical to that specified in Eqs.(6)–(7), in order to obtain the capacitively-determined frequency-dependent dielectric permittivity, $\epsilon'_{E,b}(f_i)$, i=1, . . . , K, and capacitively-determined frequency-dependent electrical conductivity $\sigma'_{E,b}(f_i)$, i=1, . . . , K, real functions associated with the bony member. Alternatively, the bone-admittance data may be processed directly, either alone or in conjunction with the reference-admittance data, either by use of a neural network or by least-squares regression procedures as described in the previous paragraph. In cases where a reference measurement is not used, measurements of the electrode spacing, d, and electrode area, A, may also be used in the overall regression analyses. For example, if the measured bone-admittance function is $Y_{E,b}(f_i)$, i=1, . . . , K, and a reference-admittance function is not obtained, then the K frequency values of the bone-admittance function may serve directly as inputs to a neural network configured appropriately to estimate one or more of the desired bone quantities. Additionally, the electrode spacing and area may also serve as inputs along with the bone-admittance values to the neural network. Alternatively, the bone admittance values may first be scaled with an appropriate form factor, i.e., divided by F, where F=A/d, and then input to a neural network for processing. The scaled or unscaled bone-admittances may also be curve fit by a regression equation and the regression coefficients used to identify the bone quantity of interest, either through use of a neural network or a least-squares regression approach. These alternative variations of the embodiments are depicted in the flow chart of FIG. 4.

Figure 5:
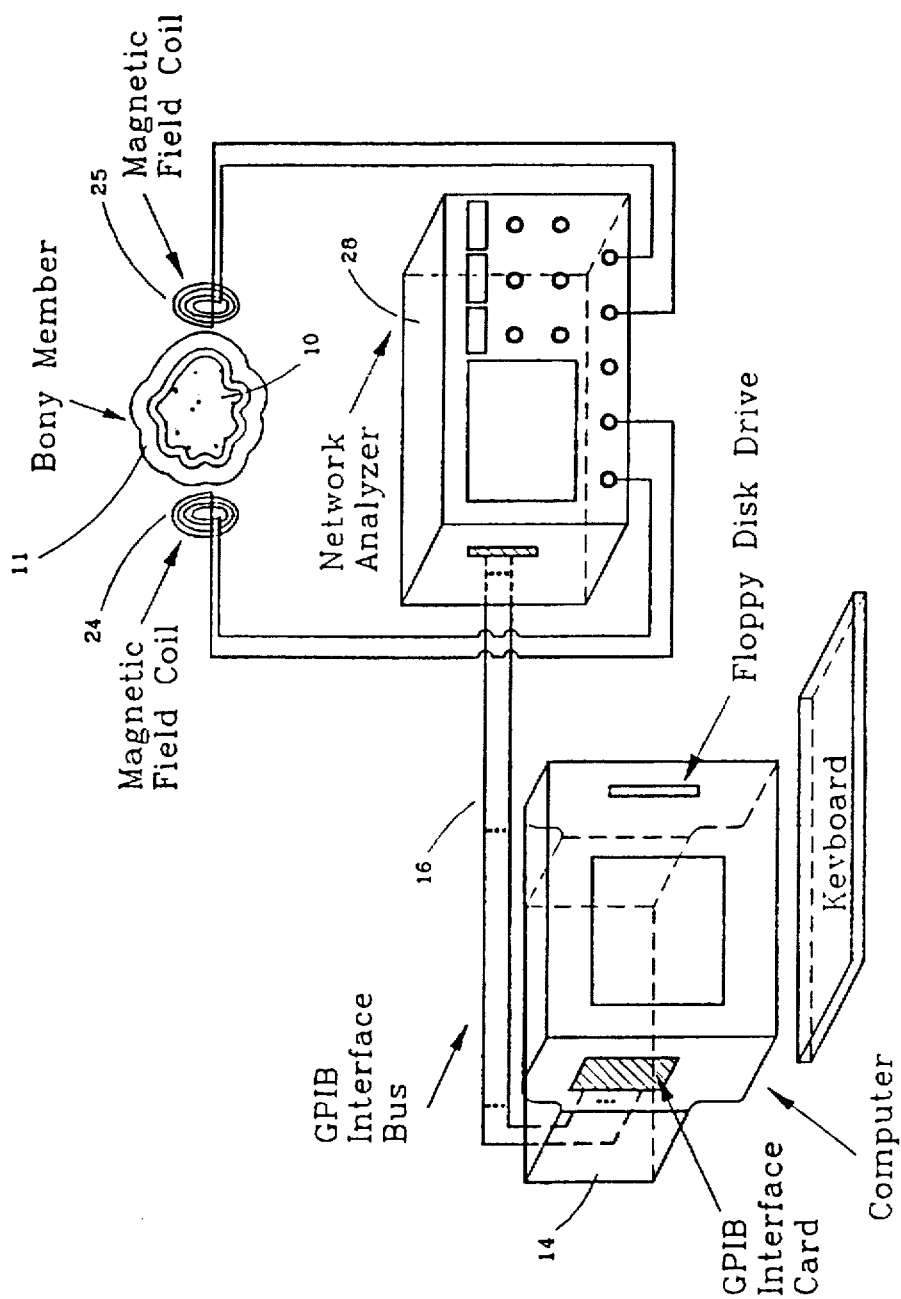
FIG. 5 is an electrical-circuit diagram schematically showing the interconnected relation of components of apparatus of the invention, but for another embodiment.
Figure 6:
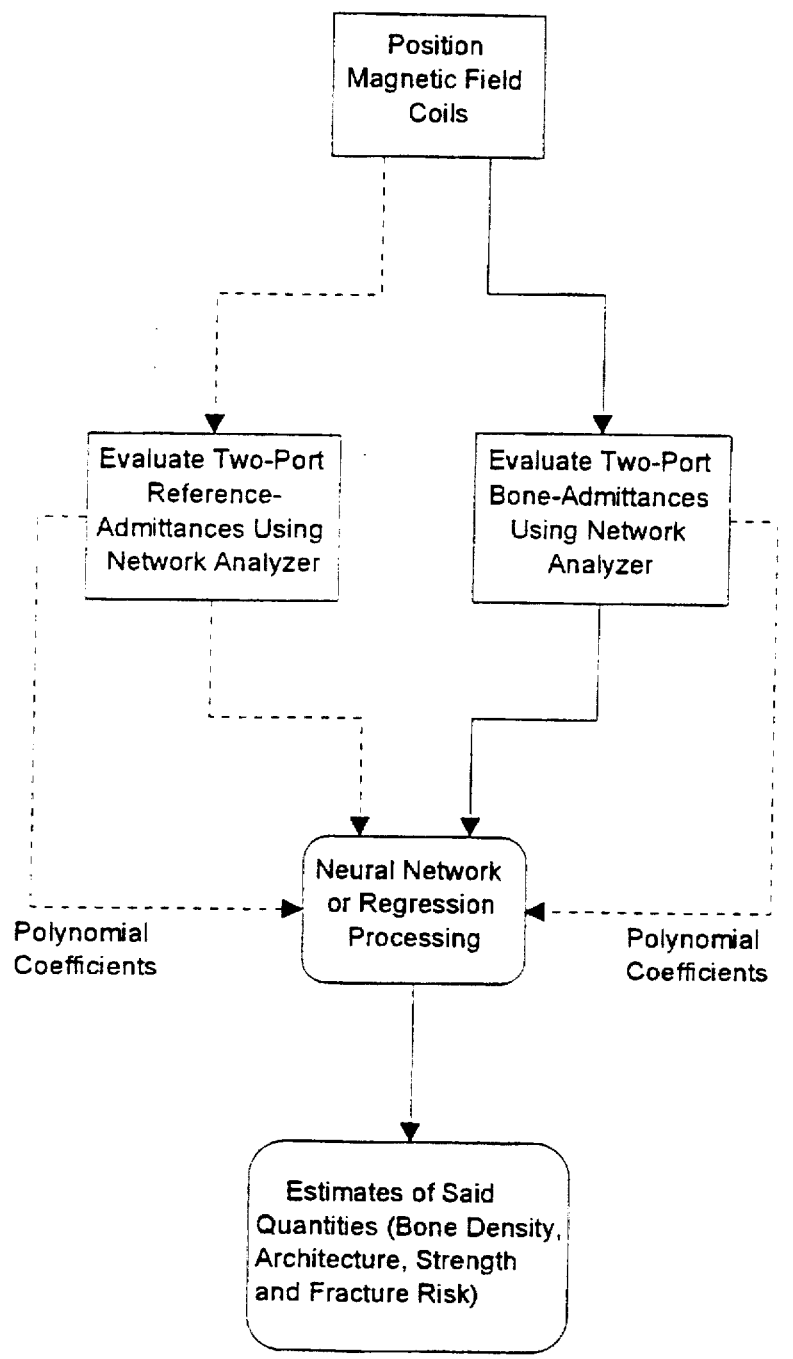
FIG. 6 is a flow chart of computer-controlled operations associated with FIG. 5, in automatically analyzing and quantitatively reporting estimates of relevant bone properties.

In yet an alternative embodiment and with additional reference to FIG. 5, the electrical elements may each be cylindrical magnetic field coils 24, 25, placed on either side of the bony member 10, 11. The magnetic field coils 24, 25 in this embodiment may each have a diameter of 1 centimeter, and each be composed of 25 turns of No. 20 magnet wire. An electronic caliper (not shown), most suitably a Mitutoyo Model No. 610-0038, available from Eastern Tool and Supply Co., (New York, N.Y.), may be used to measure the separation distance between the magnetic field coils 24, 25. An additional reference measurement made on a medium of known length and electromagnetic properties, most suitably air, is also acquired. The reference measurement should be made at a specified magnetic coil separation distance, most suitably at the same separation distance as that used in the measurement of the bony member. In this alternative embodiment, an electrical network analyzer 28 may be used to carry out the full two-port identification of the magnetic field coils-bony member system. The network analyzer 28 may suitably be a Hewlett-Packard (Santa Clara, Calif.) Model No. 8751A. The network analyzer performs the complete identification of a linear two-port network, in this case that comprised of the two magnetic field coils and interposed media, i.e., either the bony member or air. The frequency range of the network analyzer is 5 Hz to 500 MHz. Two sets of data are acquired in this embodiment of the invention, namely an inductively-determined (i.e., with the magnetic field coils) bone-admittance data set, $\{Y_{M,b11}(f_i), Y_{M,b12}(f_i), Y_{M,b22}(f_i), i=1, \ldots, K\}$, and an inductively-determined reference-admittance data set, $\{Y_{M,r11}(f_i), Y_{M,r12}(f_i), Y_{M,r22}(f_i), i=1, \ldots, K\}$. These two sets of inductively-determined admittance functions are notated by a subscript "$_M$" to indicate that they are obtained with the set of magnetic field coils and that they are distinct from the capacitively-determined bone-admittance and reference-admittance functions measured with the electrodes in another embodiment of the invention. These inductively-determined admittance functions are measured by the network analyzer 28 and then uploaded via the GPIB 16 to the computer 14 for further processing. In a presently preferred embodiment, the inductively-determined bone-admittance data and inductively-determined reference-admittance data sets serve as the inputs to an appropriately configured neural network to generate an estimate of one or more of the above-indicated and currently analyzed bone properties. In several variations of this presently preferred embodiment, specific subsets of the inductively determined bone-admittance data set may be processed either alone or in conjunction with specific subsets of the inductively-determined reference-admittance data set, either by use of a neural network or with use of least-squares regression procedures. For example, in a currently preferred embodiment, K=10 values of the inductively-determined bone-admittance function, $Y_{M,b12}(f_i)$, i=1, ..., K=10, with $f_1$=10 kHz, $f_2$=50 kHz, $f_3$=150 kHz, $f_4$=450 kHz, $f_5$=850 kHz, $f_6$=1.6 MHz, $f_7$=4 MHz, $f_8$=10 MHz, $f_9$=25 MHz and $f_{10}$=50 MHz, are used and serve directly as inputs to a neural network configured appropriately to estimate bone mineral density. In yet another alternative embodiment, the inductively determined bone-admittance data $Y_{M,b12}(f_i)$, i=1, ..., K, is curve fit by a second-order regression equation and the regression coefficients are used to identify the bone density, through use of a first-order linear least-squares regression approach. These variations and alternative embodiments of the invention which incorporate magnetic field coils are depicted in the flow chart of FIG. 6.

An important aspect of the current invention is the discovery that the electrode (capacitive-coupling) and magnetic field coil (inductive-coupling) techniques provide independent and distinct characterizations of the bony member. This novel finding is based on the facts that (1) the bony member is a heterogeneous (multi-phase) medium and (2) that each electromagnetic interrogation method interacts distinctly with respect to the interfaces within the heterogeneous bony member. To further explain this concept, suppose a heterogeneous medium (like trabecular bone for example) is composed of two materials, namely a fluid, F, and a solid, S, and that it is exposed to an exogenous electromagnetic field. A Poynting "mixture" formula can be derived for the effective complex electrical conductivity, $\sigma_{\mathit{eff}}$, of the composite medium:

$$\sigma_{\mathit{eff}} \equiv \frac{\sigma_F \int_{V_F} E_F \cdot E_F^* dv + \sigma_S \int_{V_S} E_S \cdot E_S^* dv}{\int_V E \cdot E^* dv} \tag{9}$$

where $\sigma_F$ and $\sigma_S$ are complex conductivities associated with the fluid and solid phases, respectively. $E_F$ and $E_S$ are complex electric field vectors associated with the fluid and solid phases, respectively. $V_F$ and $V_S$ are the fluid and solid volumes, respectively, over which the integrations in the numerator are carried out, and the denominator is a normalization factor for which the integration is carried out over the entire medium volume, V, for the electric field vector, E. (It should be understood that the complex conductivities ($\sigma_F$, for example), are directly related by a factor, $j\omega$, to associated complex permittivities ($\sigma_F = j\omega\epsilon_F$, for example), and also to associated real permittivities and real conductivities ($\epsilon_F = \epsilon'_F + \sigma'_F/(j\omega)$, for example, where $\epsilon'_F$ is the real dielectric permittivity and $\sigma'_F$ is the real electrical conductivity associated with the fluid phase.) Similar notations are used throughout this disclosure and should also be understood by the context whether real or complex permittivities and/or conductivities are implied.) Note that * denotes complex conjugate. The electric and magnetic fields can be expressed as functions of a vector magnetic potential, $A_i$, and a scalar electric potential, $\phi_i$, and where i=F,S:

$$B_i = \nabla \times A_i \tag{10}$$

$$E_i = -\nabla \phi_i - \frac{\partial A_i}{\partial t} \tag{11}$$

with an appropriate boundary condition:

$$n \cdot (\sigma_F \nabla \phi_F - \sigma_S \nabla \phi_S) = j\omega(\sigma_S - \sigma_F) A \cdot n \tag{12}$$

In Eq. (12), n is a unit vector normal to the interface between medium S and medium F. A is the assumed known exogenous vector magnetic potential, and ω is the radian frequency. The boundary condition, Eq. 12, clarifies the fact that the electrode (i.e., capacitive) characterization (in which $A_i \approx 0$, i=F,S) will produce an effective complex conductivity, say $\sigma_{E,\text{eff}}$ different from the magnetic field coil (i.e., inductive) characterization (in which $A_i \neq 0$, i=F,S), which produces an effective complex conductivity, say $\sigma_{M,\text{eff}}$ such that $\sigma_{E,\text{eff}} \neq \sigma_{M,\text{eff}}$ (It should be understood that in this particular example the frequency is assumed to be relatively low, so that the induced fields in the composite material may be assumed small with respect to the exogenous fields, although the results of this section may be understood to apply throughout the preferred range of frequencies. Thus in this case the exogenous magnetic vector potential, A, is assumed to be unperturbed by the currents induced to flow in the composite medium. It should further be understood that the exogenous vector magnetic potential, A, is continuous across any interface, and thus a subscript i=F or i=S is not explicitly used in the boundary condition (Eq. 12) above.)

As a specific example of the above and to further illustrate the essential uniqueness of the electrode and magnetic field coils characterizations, it is useful to consider a set of spheres of complex conductivity, $\sigma_S$, embedded in a medium of complex conductivity, $\sigma_F$. In this case, one can analytically evaluate the effective complex conductivity, $\sigma_{E,\text{eff}}$ and the effective complex conductivity, $\sigma_{M,\text{eff}}$ in closed form, obtaining $$\sigma_{M,\text{eff}} = \sigma_{E,\text{eff}} \left| 1 + \phi_S \frac{\sigma_F - \sigma_S}{\sigma_S + 2\sigma_F} \right|^2 \tag{13}$$

Eq. (13) shows for a particular case the uniqueness of the electrode and magnetic field coil characterizations of a heterogeneous material, and demonstrates the general result that $\sigma_{E,\text{eff}}$ and $\sigma_{M,\text{eff}}$ are distinct and include additional information in relation to each other.

With respect to the current invention, the above analysis provides the basis for using the electrode (i.e., capacitively) determined bone-admittance function, $Y_{E,b}(f)$, and the magnetic field coil (inductively) determined bone-admittance functions, $Y_{M,b11}(f)$, $Y_{M,b12}(f)$, $Y_{M,b22}(f)$, in conjunction with one another (with or without the associated reference-admittance functions). Since bone tissue has numerous interfaces between the bone phase and marrow phase per se, and since the bony member itself has numerous interfaces between the distinct tissue types (e.g., cortical and trabecular bone), the electrode (capacitive) measurements and magnetic field coil (inductive) measurements provide characterizations that are distinct from one another. The advantages associated with using electrode bone-admittance data together with magnetic field coil bone-admittance data are the improved accuracy and precision with which the bone properties of interest may be estimated, namely, bone mineral density, architecture, strength, and/or fracture risk.

Figure 7:
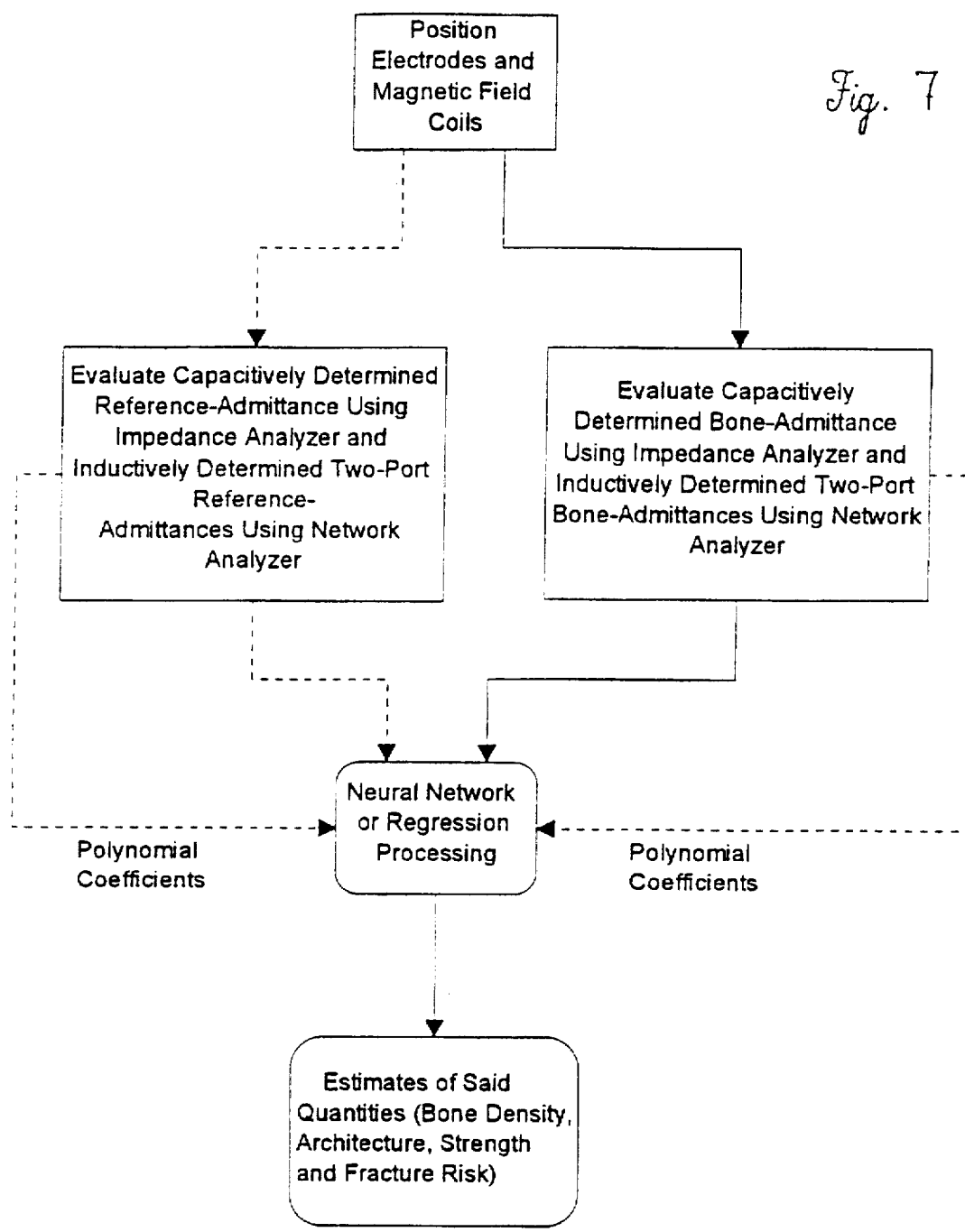
FIG. 7 is an additional flow chart of computer-controlled operations associated with FIG. 3 and FIG. 5, in automatically analyzing and quantitatively reporting estimates of relevant bone properties.

In one such presently preferred embodiment of the invention, the capacitively-determined bone-admittance magnitude function $|Y_{E,b}(f_k)|$, k=1, . . . , 12, $f_1$=200 Hz, $f_2$=1200 Hz, $f_3$=2500 Hz, $f_4$=5000 Hz, $f_5$=10 kHz, $f_6$=25 kHz, $f_7$=50 kHz, $f_8$=125 kHz, $f_9$=400 kHz, $f_{10}$=1 MHz, $f_{11}$=4 MHz and $f_{12}$=10 MHz, and inductively-determined bone-admittance magnitude function, $|Y_{M,b12}(f_i)|$, i=1, . . . , 10, $f_1$=10 kHz, $f_2$=50 kHz, $f_3$=150 kHz, $f_4$=450 kHz, $f_5$=850 kHz, $f_6$=1.6 MHz, $f_7$=4 MHz, $f_8$=10 MHz, $f_9$=25 MHz and $f_{10}$=50 MHz, serve as 22 inputs to an appropriately configured neural network in order to estimate one or more of the currently analyzed bone properties. This and other variations of the embodiments, including regression based analyses, are depicted in the flow chart of FIG. 7.

Figure 8:
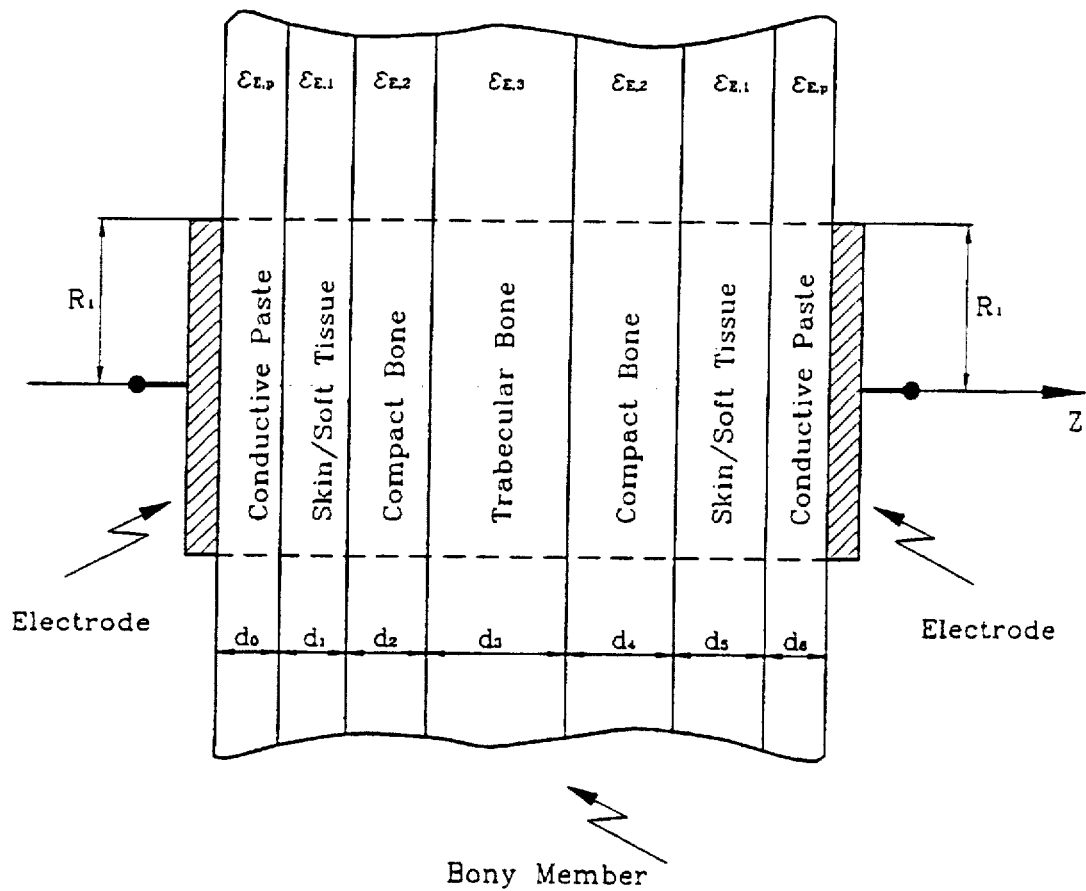
FIG. 8 is a schematic diagram of the electrodes in contact with the bony member, showing additional details of the invention portrayed in FIG. 1 and FIG. 3.
Figure 9:
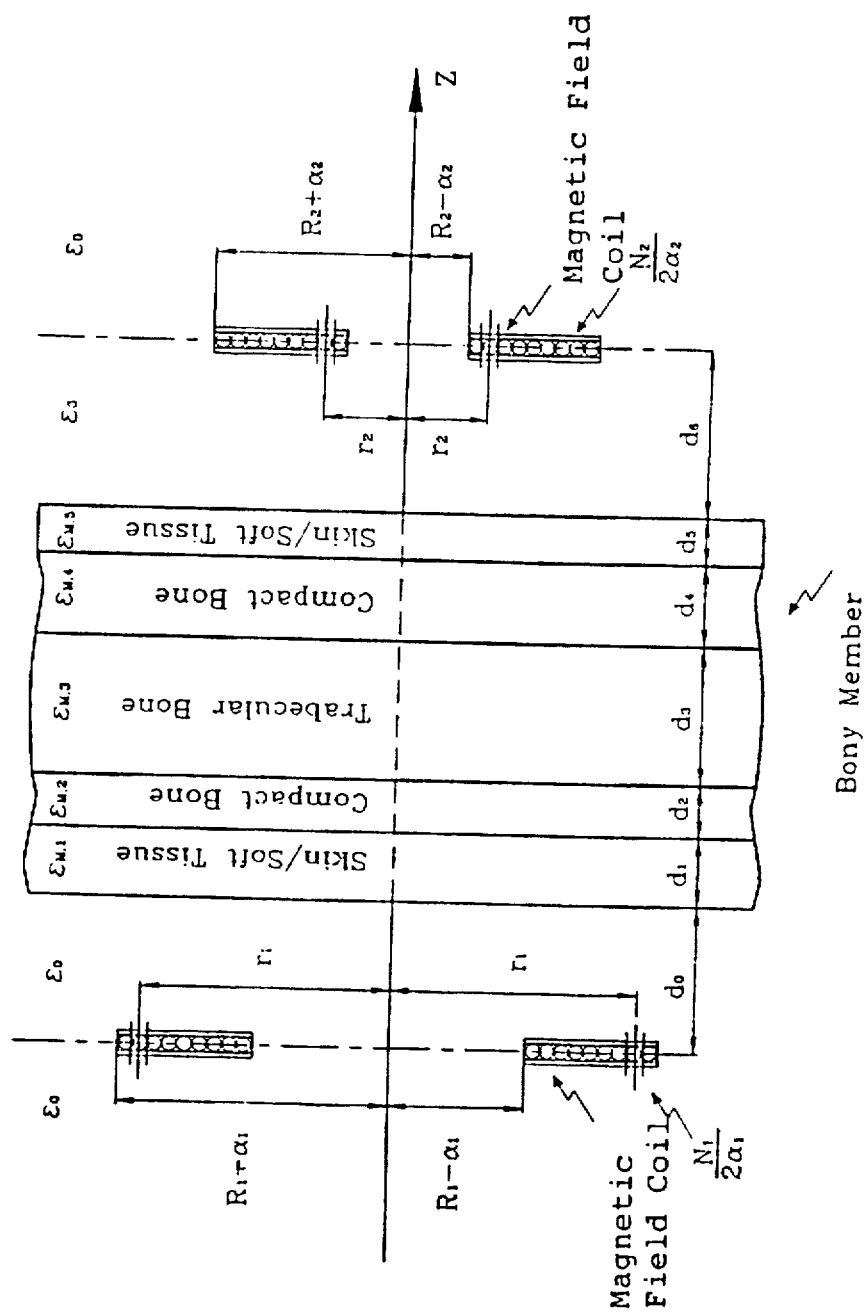
FIG. 9 is a schematic diagram of the magnetic field coils overlying the bony member, showing additional details of the invention portrayed in FIG. 5.

Considering the above electrode and magnetic field coil characterizations, more detailed schematic depictions of two embodiments of the invention are shown in FIG. 8 and FIG. 9. These figures contain characterizations of the bony member shown in FIG. 1, FIG. 3, and FIG. 5. In FIG. 8, a portion of the bony member consisting of layers of skin (soft tissue), compact (cortical) bone and trabecular bone is shown in electrical contact with two electrodes (i.e., capacitive coupling). The complex capacitively-determined admittance function of the bony member, $Y_{E,b}(f_i)$, i=1, . . . , K, is given by $$Y_{E,b}(f_i) = \tag{14}$$

$$K_E \left[ \frac{d_0}{\epsilon_{E,p}} + \frac{d_1}{\epsilon_{E,1}} + \frac{d_2}{\epsilon_{E,2}} + \frac{d_3}{\epsilon_{E,3}} + \frac{d_4}{\epsilon_{E,2}} + \frac{d_5}{\epsilon_{E,1}} + \frac{d_6}{\epsilon_{E,p}} \right]^{-1}$$

where $$K_E = j2\pi^2 f_i R_1^2 \tag{15}$$

and where $\epsilon_{E,p}$, $\epsilon_{E,1}$, $\epsilon_{E,2}$ and $\epsilon_{E,3}$ are the complex dielectric permittivities associated with electrode (i.e., capacitive) characterizations of the conductive paste, skin (soft tissue) layer, compact (cortical) bone, and trabecular bone, respectively; $d_0$ and $d_6$ are the respective thicknesses of the two conducting paste layers, $d_1$ and $d_5$ are the respective thicknesses of the two skin (soft tissue) layers, $d_2$ and $d_4$ are the respective thicknesses of the two cortical (compact) bone layers, $d_3$ is the thickness of the trabecular bone within the bony member, and $R_1$ is the radius of each circular electrode. It should be understood that the permittivities have a subscript "$_E$", to indicate that they are based on electrode (capacitive) measurements, in contrast to that which would be evaluated in case of magnetic field coil (inductive) measurements, as described in the next paragraph. It should be further understood that each of the said permittivity functions is a complex permittivity function described by $$\epsilon_{E,i} = \epsilon'_{E,i} + \frac{\sigma_{E,i}'}{j\omega} \tag{16}$$

where $\epsilon'_{E,i}$ and $\sigma'_{E,i}$ are the real dielectric permittivity and real electrical conductivity of medium i, respectively, and i=p,1,2,3.

In contrast to FIG. 8, FIG. 9 shows two magnetic field coils (i.e., inductive coupling) surrounding a portion of the bony member, which consists as before of layers of skin (soft tissue), compact (cortical) bone and trabecular bone. In this case, however, $\epsilon_{M,0}$, $\epsilon_{M,1}$, $\epsilon_{M,2}$ and $\epsilon'_{M,3}$ are the complex dielectric permittivities of free-space, skin (soft tissue layer), compact (cortical bone layer), and trabecular bone layer, respectively, when magnetic field coils are used to (inductively) characterize the bony member. Note that $\epsilon_{M,4} = \epsilon_{M,2}$ and $\epsilon_{M,5} = \epsilon_{M,1}$.

The set of two-port admittance functions associated with the bony member, $\{Y_{M,b11}(f_i), Y_{M,b12}(f_i), Y_{M,b22}(f_i), i=1, . . . , K\}$, and which is measured with a network analyzer as shown in FIG. 5 is directly related to the inductances and mutual inductances associated with the two magnetic field coils and enclosed bony member. These inductances and mutual inductance can be explicitly derived and are presented here. Let $$\chi_i^2 = \omega^2 \mu_0 \epsilon_{M,i} \tag{17}$$

-continued and $$p_i = \sqrt{q^2 - \chi_i^2} \qquad (18)$$

i=0,1,2,3,4,5, where q is a dummy variable, $0 \leq q < \infty$, such that $Re[p_i] > 0$, and $\mu_0$ is the magnetic permeability of free space. Note that $\epsilon_{M,0}$ is equal to the permittivity of free space, i.e., $\epsilon_{M,0} = \epsilon_0$. For each value of $\omega$ (in the presently preferred embodiment, $0 \leq \omega \leq 2\pi \cdot 200$ MHz) and for each value of q, the following set of equations are evaluated:

$$a_5 = \frac{1}{2} e^{-p_5 d_5} \left( 1 - \frac{p_0}{p_5} \right) \qquad (19)$$

$$b_5 = \frac{1}{2} e^{p_5 d_5} \left( 1 + \frac{p_0}{p_5} \right) \qquad (20)$$

$$a_4 = \frac{1}{2} e^{-p_4 d_4} \left[ a_5 + b_5 - \frac{p_5}{p_4} (b_5 - a_5) \right] \qquad (21)$$

$$b_4 = \frac{1}{2} e^{p_4 d_4} \left[ a_5 + b_5 + \frac{p_5}{p_4} (b_5 - a_5) \right] \qquad (22)$$

$$a_3 = \frac{1}{2} e^{-p_3 d_3} \left[ a_4 + b_4 - \frac{p_4}{p_3} (b_4 - a_4) \right] \qquad (23)$$

$$b_3 = \frac{1}{2} e^{p_3 d_3} \left[ a_4 + b_4 + \frac{p_4}{p_3} (b_4 - a_4) \right] \qquad (24)$$

$$a_2 = \frac{1}{2} e^{-p_2 d_2} \left[ a_3 + b_3 - \frac{p_3}{p_2} (b_3 - a_3) \right] \qquad (25)$$

$$b_2 = \frac{1}{2} e^{p_2 d_2} \left[ a_3 + b_3 + \frac{p_3}{p_2} (b_3 - a_3) \right] \qquad (26)$$

$$a_1 = \frac{1}{2} e^{-p_1 d_1} \left[ a_2 + b_2 - \frac{p_2}{p_1} (b_2 - a_2) \right] \qquad (27)$$

$$b_1 = \frac{1}{2} e^{p_1 d_1} \left[ a_2 + b_2 + \frac{p_2}{p_1} (b_2 - a_2) \right] \qquad (28)$$

The mutual ($M_{12}$) and self inductance ($L_{11}$) are evaluated using:

$$M_{12} = K_1 \int_{R_1-\alpha_1}^{R_1+\alpha_1} r_1 dr_1 \int_{R_2-\alpha_2}^{R_2+\alpha_2} r_2 dr_2 \int_0^\infty \frac{qJ_1(qr_1)J_1(qr_2)e^{-p_0(d_0+d_6)}}{[(a_1-b_1)p_1 - (a_1+b_1)p_0]} dq \qquad (29)$$

$$L_{11} = K_2 \int_{R_1-\alpha_1}^{R_1+\alpha_1} r_1 dr_1 \int_{R_1-\alpha_1}^{R_1+\alpha_1} r_2 dr_2 \int_0^\infty \frac{qJ_1(qr_1)J_1(qr_2)\Lambda_1 e^{-p_0 d_0}}{[(a_1-b_1)p_1 - (a_1+b_1)p_0]} dq \qquad (30)$$

where $$\Lambda_1 = \left[ (a_1 + b_1)\cosh(p_0 d_0) - \frac{p_1}{p_0}(a_1 - b_1)\sinh(p_0 d_0) \right] \qquad (31)$$

$$K_1 = \mu_0 \frac{2\pi N_1 N_2}{4\alpha_1 \alpha_2} \qquad (32)$$

and $$K_2 = \mu_0 \frac{2\pi N_1^2}{4\alpha_1^2} \qquad (33)$$

Analogous equations hold for $L_{22}$ and $M_{21}$. In Eqs. (29)–(33), $N_1/(2\alpha_1)$ and $N_2/(2\alpha_2)$ are the number of loops per unit length of the coils adjacent to the skin shown on the left side and the right side of FIG. 9, respectively. $J_1(r)$ is the real Bessel function of order 1, and the variables representing the size and locations of the coils (i.e., $R_1$, $R_2$, $\alpha_1$ and $\alpha_2$) are as shown in FIG. 9.

The above equations, namely, Eqs. (14)–(16) for the electrode measurements, and Eqs. (17)–(33) for the magnetic field coil measurements, demonstrate explicitly how the underlying electrical properties of the bony member are manifested in the measured bone-admittance functions. It should therefore be understood that the respective bone-admittance functions, namely $\{Y_{E,b}(f_i), i=1, \ldots, K\}$, for the electrode measurements and $\{Y_{M,b11}(f_i), Y_{M,b12}(f_i), Y_{M,b22}(f_i), i=1, \ldots, K\}$ for the magnetic field coil measurements, contain information which is used to generate the indicated estimates of the status of bone that is currently being analyzed. It should further be understood that the information contained in the electrode and magnetic field coil measurements are distinct from one another, and therefore may be used in conjunction with one another to improve the accuracy and precision of the indicated estimates of bone status. As noted, these variations of the embodiments are depicted in the flow chart of FIG. 7.

Figure 10:
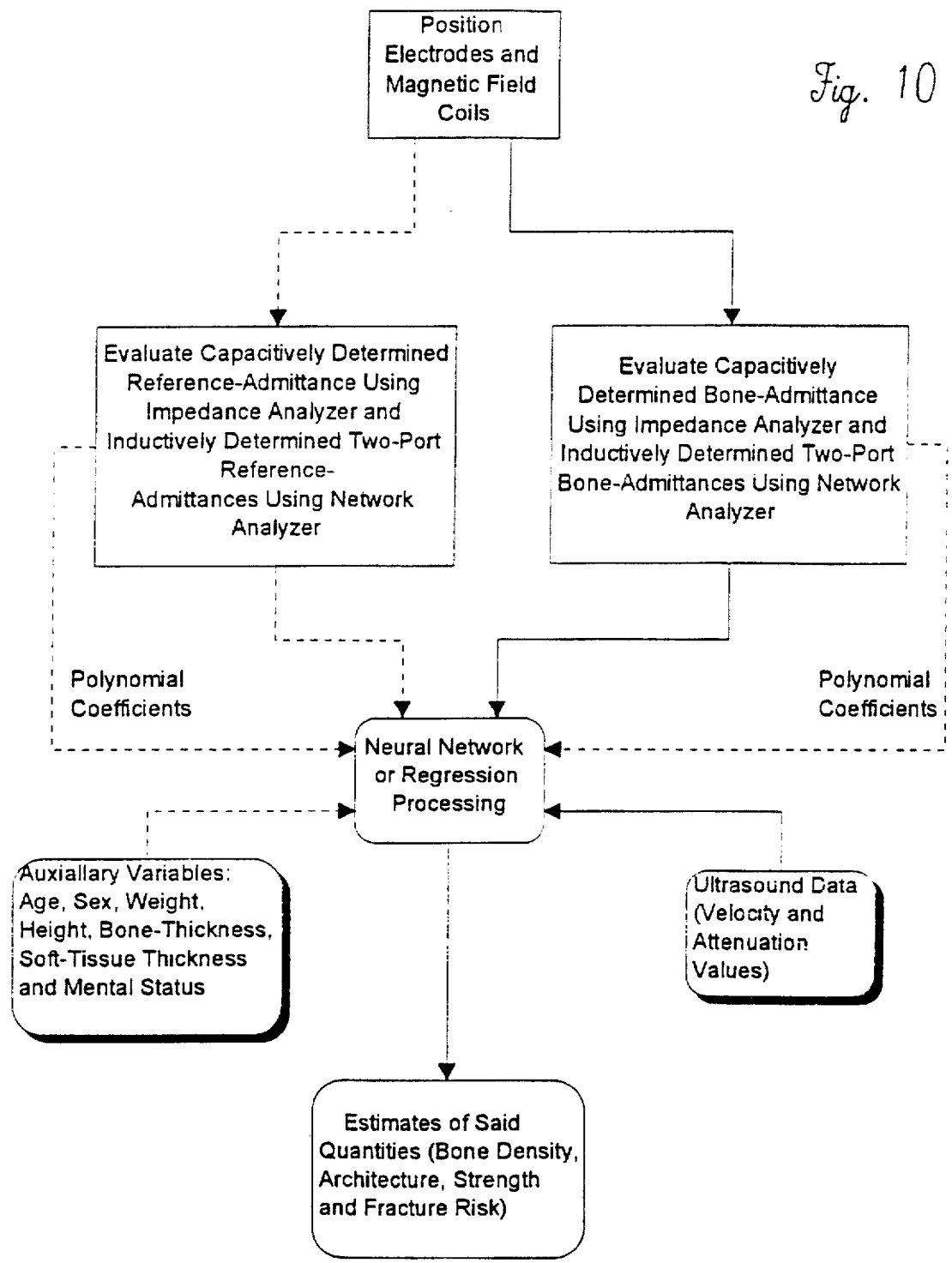
FIG. 10 is an additional flow chart of computer-controlled operations associated with another embodiment which uses both ultrasonic and electromagnetic measurement data to automatically analyze and quantitatively report estimates of relevant bone properties.

In one yet further and alternative embodiment of the present invention, and with additional reference to the flow chart of FIG. 10, the electromagnetic (electrode and magnetic field coil) measurements are used in conjunction with ultrasonic data to more accurately determine bone density, architecture, strength, and fracture risk. Standard ultrasonic measurements of acoustic velocity and attenuation are carried out on the same bony member evaluated electromagnetically. Details of this ultrasonic technique may be found in U.S. Pat. No. 5,259,384 entitled "Ultrasonic Bone-Assessment Apparatus and Method" dated Nov. 9, 1993, the entire disclosure of which is incorporated herein by reference. In this alternative embodiment, the ultrasonic velocity and attenuation are used in conjunction with the electrode and/or magnetic field coils admittance functions, which are all input to an appropriately configured neural network to generate an estimate of the status of bone that is currently being analyzed. For example, in one currently preferred embodiment a feedforward neural network consisting of 12 inputs, one hidden layer with 20 units, and one output is configured to generate an estimate of the risk (i.e., probability) of bone fracture. The twelve (12) inputs to the neural network are the ultrasonic velocity (in meter/sec) ultrasonic differential attenuation (in $dBcm^{-1}$ $MHz^{-1}$), five (5) magnitude values of the capacitively-determined (electrode) bone-admittance function normalized by the capacitively-determined (electrode) reference admittance function, i.e., $|Y_{E,b}(f_i')/Y_{E,r}(f_i')|$, i=1, ..., 5, (dimensionless) and five (5) magnitude values of the inductively-determined (magnetic field coils) bone-admittance function, i.e., $|Y_M$, $b_{12}(f_i'')|$, i=1, ..., 5 ($\Omega^{-1}$). The frequencies, $f_i'$, i=1, ..., 5, are 10 Hz, 1000 Hz, 10,000 Hz, 50,000 Hz and 200,000 Hz; the frequencies, $f_i''$, i=1, ..., 5, are 25,000 Hz, 125,000 Hz, 875,000 Hz, 2.5 MHz and 25 MHz.

For further understanding of the utility of combining electromagnetic measurements with ultrasonic data, it is useful to consider a specific structural model of trabecular bone. The model consists of a regular arrangement of fundamental cubic cells or "rooms" surrounded by porous "walls." The walls have a thickness, d, and a length, l, and the average total area of the pores in any one wall is equal to P. The walls (excluding their pores) have a complex conductivity, $\sigma_S$, and the material which fills all the pores of the model has a complex conductivity, $\sigma_F$. Using Maxwell mixture theory, it can be shown that the reciprocal of the effective complex conductivity, $1/\sigma_{\it{eff}}$, of the overall bone model structure is given by $$\frac{1}{\sigma_{\it{eff}}} = \frac{1-b}{\sigma_F(1-b)^2 + 2\sigma_2 b(1-b)} + \frac{b}{\sigma_1} \quad (34)$$

where $$\sigma_1 = \sigma_S(1-a) + \sigma_F a \quad (35)$$

$$\sigma_2 = \sigma_S \frac{1 + a\frac{\sigma_F - \sigma_S}{\sigma_F + \sigma_S}}{1 - a\frac{\sigma_F - \sigma_S}{\sigma_F + \sigma_S}} \quad (36)$$

and where $a=P/l^2$ and $b=d/l$. The porosity, $\phi$, of the trabecular bone model is given by $$\phi = (1-b)^3 + 3ab \quad (37)$$

with the constraint $a \leq (1-b)^2$.

The above example demonstrates that electromagnetic measurements contains information related to the biomechanical properties of bone. The above example also shows, for this particular structural model, that bone density is a function of two (2) architectural parameters (in this case, a and b), and therefore a single type of measurement (electrode or magnetic field coils or ultrasonic) may not be able to accurately characterize the bone status parameters of interest. However, combining these measurements, either through an appropriately configured neural network or a least-squares regression equation, can provide the information necessary to quantitatively evaluate bone tissue in vivo, as manifested at a given time, through one or more of the quantities: bone mineral density, architecture, strength and fracture risk. As a further variation of the embodiments of the invention, the neural network or regression equations may be adapted to receive additional inputs (i.e., auxiliary data) selected from the group comprising: age, sex, weight, height, bone-tissue thickness, soft-tissue thickness and mental status. The flow chart in FIG. 10 details several alternative embodiments associated with the combination of ultrasonic, electromagnetic and auxiliary data.

The foregoing discussion for the variations and embodiments of FIGS. 1–10 has demonstrated both digital and analog techniques. It will be understood, therefore, that the respective embodiments and their variations can be implemented through either digital or analog techniques.

It will be seen that the described invention meets all stated objectives as to evaluation of the status of bone tissue in vivo, with specific advantages that include but are not limited to the following:

(1) Broadband pulse excitations which provide an extremely large bandwidth over which to examine the electrical properties of the bone tissue. This allows a great deal of information on the bony member to be more obtained through identification of the frequency-dependent admittance functions (obtained with electrodes and/or magnetic field coils). Direct measurements of the (capacitively-determined) electrical bone-conductivity real function, $\sigma'_{E,b}(f)$, and frequency-dependent dielectric bone-permittivity real function, $\epsilon'_{E,b}(f)$, associated with the bony member, can also be obtained;

(2) Incorporation of as much information as is available from linear electromagnetic measurement data, which includes using both the frequency-dependent electrical bone-conductivity real function, $\sigma'_{E,b}(f)$, and frequency-dependent relative dielectric bone-permittivity real function, $\epsilon'_{E,b}(f)$, and taking into account the nonlinear frequency-dependence of the complex dielectric functions through appropriate least-squares regressions;

(3) Use of both capacitively-derived (i.e., electrode) bone-admittance function data, $Y_{E,b}(f)$, as well as inductively-derived (i.e., magnetic field coils) bone-admittance function data, $\{Y_{M,b11}(f), Y_{M,b12}(f), Y_{M,b22}(f)\}$, which due to the heterogeneous nature of trabecular bone as well as the multi-layered nature of the bony member itself comprised of soft tissue, cortical bone and trabecular bone, provide independent features related to the desired properties of bone being analyzed;

(4) Use of a specific calibration technique through means of reference measurements to determine the actual electrical properties of the bony member, as for example, through identification of the geometric form factor associated with the electrode configuration;

(5) Combining both electromagnetic data (bone-admittance and/or permittivity and conductivity functions) with ultrasonic measurements, which provides for increased accuracy and precision of the bone property estimates, due to the multi-factorial nature of bone and related bone status parameters;

(6) Sophisticated analysis of the data, in contrast to the prior art which relies largely on simplistic univariate linear regression. In contrast, the processing described relies on neural network technology, which provides multivariate nonlinear analysis to determine the density, architecture, strength, and/or fracture risk of bone. This approach also may be regularly updated and improved, as more data becomes available;

(7) The nature of the apparatus as described here serves best the purposes of further experimentation and exploration for obtaining accurate electromagnetic bone data that can be correlated for the indicated objectives. The embodiments of the invention as described above can explore a wide range of experimental configurations. Their use is expected to lead to the development of compact and efficient apparatus for obtaining the indicated objectives. For example, an analog implementation can easily be constructed if economy and simplicity are the primary objectives. Other systems which rely on analog-to-digital converters are more expensive, yet can be more flexible in terms of the type of processing which can be performed. Either type of system can either be built as a stand-alone unit or as part of a PC-based system.

What is claimed is:

1. Apparatus for non-invasive quantitative evaluation of the status of bone tissue in vivo, as measured in a selected bony member of a living body and manifested through one or more of the quantities: bone-mineral density, architecture, strength and fracture risk at a given time, said apparatus comprising:

- circuit means including a pair of spaced magnetic field coils wherein the spacing is adapted to receive the bony member to be analyzed and wherein said circuit means is a two-port electrical circuit,
- network analyzer means included in said circuit means for obtaining a set of three (3) inductively-determined two-port frequency-dependent bone-admittance functions when said circuit means includes said bony member;
- means for selectively using said pair of magnetic field coils and said network analyzer with a medium of known electrical and magnetic properties and path length to thereby establish a set of three (3) inductively-determined two-port frequency-dependent reference-admittance functions, and including means to store each of said reference-admittance functions, and
- means for comparatively evaluating said bone-admittance functions and reference-admittance functions, whereby to estimate one or more of the said quantities.

2. Apparatus for non-invasive quantitative evaluation of the status of bone tissue in vivo, as measured in a selected bony member of a living body and manifested through one or more of the quantities: bone-mineral density, architecture, strength and fracture risk at a given time, said apparatus comprising:

- circuit means including a pair of spaced magnetic field coils wherein the spacing is adapted to receive the bony member to be analyzed and wherein said circuit means is a two-port electrical circuit,
- network analyzer means included in said circuit means for obtaining a set of three (3) inductively-determined two-port frequency-dependent bone-admittance functions when said circuit means includes said bony member, and
- means for comparatively evaluating said bone-admittance functions, whereby to estimate one or more of the said quantities.

3. Apparatus for non-invasive quantitative evaluation of the status of bone tissue in vivo, as measured in a selected bony member of a living body and manifested through one or more of the quantities: bone-mineral density, architecture, strength and fracture risk at a given time, said apparatus comprising:

- circuit means including a pair of spaced magnetic field coils wherein the spacing is adapted to receive the bony member to be analyzed and wherein said circuit means is a two-port electrical circuit,
- network analyzer means included in said circuit means for obtaining a set of three (3) inductively-determined two-port frequency-dependent bone-admittance functions when said circuit means includes said bony member;
- means for selectively using said pair of magnetic field coils and said network analyzer with a medium of known electrical and magnetic properties and path length to thereby establish a set of three (3) inductively-determined two-port frequency-dependent reference-admittance functions, and including means to store each of said reference-admittance functions, and
- means including a neural network connected for response to said bone-admittance functions and reference-admittance functions, said neural network being configured to generate an estimate of one or more of the said quantities.

4. Apparatus for non-invasive quantitative evaluation of the status of bone tissue in vivo, as measured in a selected bony member of a living body and manifested through one or more of the quantities: bone-mineral density, architecture, strength and fracture risk at a given time, said apparatus comprising:

- circuit means including a pair of spaced magnetic field coils wherein the spacing is adapted to receive the bony member to be analyzed and wherein said circuit means is a two-port electrical circuit,
- network analyzer means included in said circuit means for obtaining a set of four (4) inductively-determined two-port frequency-dependent bone-admittance functions when said circuit means includes said bony member, and
- means including a neural network connected for response to said bone-admittance functions, said neural network being configured to generate an estimate of one or more of the said quantities.

5. Apparatus for non-invasive quantitative evaluation of the status of bone tissue in vivo, as measured in a selected bony member of a living body and manifested through one or more of the quantities: bone-mineral density, architecture, strength and fracture risk at a given time, said apparatus comprising:

- circuit means including a pair of spaced magnetic field coils wherein the spacing is adapted to receive the bony member to be analyzed and wherein said circuit means is a two-port electrical circuit,
- network analyzer means included in said circuit means for obtaining a set of three (3) inductively-determined two-port frequency-dependent bone-admittance functions when said circuit means includes said bony member;
- means for selectively using said pair of magnetic field coils and said network analyzer with a medium of known electrical and magnetic properties and path length to thereby establish a set of three (3) inductively-determined two-port frequency-dependent reference-admittance functions, and including means to store each of said reference-admittance functions;
- additional circuit means including a pair of spaced electrodes wherein the spacing is adapted to receive the bony member to be analyzed and wherein said additional circuit means is a two-terminal electrical circuit,
- impedance analyzer means included in said additional circuit means for obtaining a capacitively-determined frequency-dependent bone-admittance function when said additional circuit means includes said bony member;
- means for selectively using said pair of electrodes and said impedance analyzer with an additional medium of known electrical and magnetic properties and path length to thereby establish a capacitively-determined frequency-dependent reference-admittance function, and including means to store said reference-admittance function, and
- means for comparatively evaluating said capacitively-determined bone-admittance function and stored reference-admittance function, and said inductively-determined bone-admittance function and stored reference-admittance function whereby to estimate one or more of the said quantities.

6. Apparatus for non-invasive quantitative evaluation of the status of bone tissue in vivo, as measured in a selected bony member of a living body and manifested through one or more of the quantities: bone-mineral density, architecture, strength and fracture risk at a given time, said apparatus comprising:

circuit means including a pair of spaced magnetic field coils wherein the spacing is adapted to receive the bony member to be analyzed and wherein said circuit means is a two-port electrical circuit, network analyzer means included in said circuit means for obtaining a set of three (3) inductively-determined two-port frequency-dependent bone-admittance functions when said circuit means includes said bony member;

additional circuit means including a pair of spaced electrodes wherein the spacing is adapted to receive the bony member to be analyzed and wherein said additional circuit means is a two-terminal electrical circuit, impedance analyzer means included in said additional circuit means for obtaining a capacitively-determined frequency-dependent bone-admittance function when said additional circuit means includes said bony member, and means for comparatively evaluating said capacitivly-determined bone-admittance function and said inductively-determined bone-admittance function whereby to estimate one or more of the said quantities.

7. Apparatus according to claim 3, wherein each of said frequency-dependent functions, namely the inductively-determined two-port frequency-dependent bone-admittance functions and the inductively-determined two-port frequency-dependent reference-admittance functions, are processed in polynomial form involving a finite set of coefficients for each polynomial, and means for supplying polynomials' coefficients as inputs to said neural network.

8. Apparatus according to claim 4, wherein said frequency-dependent functions, namely the inductively-determined two-port frequency-dependent bone-admittance functions, are processed in polynomial form involving a finite set of coefficients for each of said polynomials, and means for supplying polynomials' coefficients as inputs to said neural network.

9. Apparatus according to any one of claims 3 and 4, wherein said neural network is adapted to receive further inputs selected from the group comprising: age, sex, weight, height, bone-tissue thickness, soft-tissue thickness, overall tissue thickness, mental status, ultrasonic velocity measurements, ultrasonic attenuation measurements, and bone-densitometric measurements.

10. Apparatus according to any one of claims 3, and 4, wherein said neural network is replaced by a multivariate least-squares regression function.

11. Apparatus according to any one of claims 1, 2, 5 and 6, wherein said means for comparative evaluation is adapted for further comparative evaluation of inputs selected from the group comprising: age, sex, weight, height, bone-tissue thickness, soft-tissue thickness, overall tissue thickness, mental status, ultrasonic velocity measurements, ultrasonic attenuation measurements, and bone-densitometric measurements.

12. The method of non-invasively and quantitatively evaluating the status of bone tissue in vivo, as manifested through one or more of the quantities: bone-mineral density, architecture, strength and fracture risk, using two magnetic field coils that are spaced to receive a bony part of a living body, which method comprises the steps of:

(a) electrically coupling said magnetic field coils to nearby skin on opposite sides of said bony part, and whereby said magnetic field coils and bony part comprise a two-port electrical network;

(b) connecting a network analyzer to the said two-port electrical network, whereby to obtain a set of three (3) inductively-determined two-port frequency-dependent bone-admittance functions associated with said two-port electrical network; and (c) comparatively evaluating the set of three (3) two-port bone-admittance functions.

\* \* \* \* \*

UNITED STATES PATENT AND TRADEMARK OFFICE
CERTIFICATE OF CORRECTION

PATENT NO.   : 5,782,763
DATED        : July 21, 1998
INVENTOR(S)  : Bianco et al.

It is certified that error appears in the above-identified patent and that said Letters Patent is hereby corrected as shown below:

Column 1, under U.S. Patent Documents, please insert --
4,548,208      10/1985   Niemi .......... 128/419 F
4,556,051      12/1985   Maurer ......... 128/1.5   --

Signed and Sealed this

Tenth Day of April, 2001

Attest:

NICHOLAS P. GODICI

Attesting Officer    Acting Director of the United States Patent and Trademark Office